US009987199B2

(12) United States Patent
Inaki et al.

(10) Patent No.: US 9,987,199 B2
(45) Date of Patent: Jun. 5, 2018

(54) DENTAL ADHESIVE COMPOSITION, DENTAL ADHESIVE PRIMER, DENTAL ADHESIVE BONDING MATERIAL, DENTAL ADHESIVECOMPOSITE RESIN, AND DENTAL ADHESIVE RESIN CEMENT

(71) Applicants: Yoshitaka Inaki, Tokyo (JP); Tomonao Shimizu, Tokyo (JP); Kouichirou Hirata, Tokyo (JP)

(72) Inventors: Yoshitaka Inaki, Tokyo (JP); Tomonao Shimizu, Tokyo (JP); Kouichirou Hirata, Tokyo (JP)

(73) Assignee: TOKUYAMA DENTAL CORPORATION, Tokyo (JP)

( * ) Notice: Subject to any disclaimer, the term of this patent is extended or adjusted under 35 U.S.C. 154(b) by 13 days.

(21) Appl. No.: 14/413,356

(22) PCT Filed: Jun. 27, 2013

(86) PCT No.: PCT/JP2013/067682
§ 371 (c)(1),
(2) Date: Jan. 7, 2015

(87) PCT Pub. No.: WO2014/010431
PCT Pub. Date: Jan. 16, 2014

(65) Prior Publication Data
US 2015/0190313 A1 Jul. 9, 2015

(30) Foreign Application Priority Data
Jul. 10, 2012 (JP) ................. 2012-154602

(51) Int. Cl.
*A61K 6/00* (2006.01)
*A61K 6/083* (2006.01)
(52) U.S. Cl.
CPC ................... *A61K 6/0023* (2013.01)
(58) Field of Classification Search
None
See application file for complete search history.

(56) References Cited

U.S. PATENT DOCUMENTS

| | | | | |
|---|---|---|---|---|
| 4,271,283 A * | 6/1981 | Puhk | ............... | C08F 222/1006 526/318.3 |
| 4,303,924 A * | 12/1981 | Young, Jr. | ............. | C09D 11/101 347/100 |
| 4,383,052 A * | 5/1983 | Higo | ............. | A61K 6/0023 523/118 |
| 5,264,513 A * | 11/1993 | Ikemura | ............. | A61K 6/0023 523/116 |
| 5,767,211 A * | 6/1998 | Guan | ............. | C08F 2/38 526/171 |
| 5,886,064 A * | 3/1999 | Rheinberger | ........ | A61K 6/083 424/DIG. 16 |
| 5,925,690 A * | 7/1999 | Fuchigami | ........ | A61K 6/0088 523/118 |
| 6,387,496 B1 * | 5/2002 | Van Benthem | .... | C08G 63/6854 428/402 |
| 6,392,006 B1 * | 5/2002 | Van Benthem | .... | C08G 63/6854 428/402 |
| 6,590,070 B1 * | 7/2003 | Toriumi | .............. | C08F 4/06 428/500 |
| 7,041,711 B2 * | 5/2006 | Kunita | ............. | C07C 271/10 430/269 |
| 7,309,232 B2 * | 12/2007 | Rutherford | ............. | A61K 6/033 206/63.5 |
| 7,659,324 B2 * | 2/2010 | Moszner | ............. | A61K 6/0017 433/228.1 |
| 2002/0004900 A1 | 1/2002 | Patel | | |
| 2002/0123609 A1 * | 9/2002 | Frechet | ............. | A61K 47/48192 528/403 |
| 2003/0114553 A1 * | 6/2003 | Karim | ............. | A61K 6/0073 523/115 |
| 2004/0254260 A1 * | 12/2004 | Mikulla | ............. | A61K 6/0835 523/116 |
| 2005/0070627 A1 * | 3/2005 | Falsafi | ............. | A61K 6/0017 523/115 |
| 2006/0135719 A1 * | 6/2006 | Moszner | ............. | A61K 6/0017 526/303.1 |

(Continued)

FOREIGN PATENT DOCUMENTS

JP 6-9327 A 1/1994
JP 2000-159621 A 6/2000
(Continued)

OTHER PUBLICATIONS

Boltorn, Advancing Performacne and Comfort, Feb. 2012, no author available, pp. 1-8.*
International Search Report for International Application No. PCT/JP2013/067682, dated Oct. 1, 2013, with English translation.
"Boltorn Advancing performance & comfort", Perstorp AB, Feb. 2011; 5 pages.
Extended European Search Report corresponding to Application No. 13816481.9-1501/2873410 PCT/JP2013/067682; dated Feb. 5, 2016.
D. Slamanig et al., "Anonymous But Authorized Transactions Supporting Selective Traceability," Security and Cryptolgraphy (SECRYPT), Proceedings of the 2010 International Conference on, IEEE, Jul. 26, 2010, pp. 1-10, XP031936557.
(Continued)

Primary Examiner — Peter A Salamon
(74) Attorney, Agent, or Firm — Cantor Colburn LLP

(57) ABSTRACT

Provided are a dental adhesive composition, a dental adhesive primer, a dental adhesive bonding material, a dental adhesive composite resin, and a dental adhesive resin cement each having an excellent adhesive force and excellent adhesion durability. Specifically, provided are a dental adhesive composition, including (A) a polymerizable monomer containing an acidic group-containing polymerizable monomer, and (B) a dendritic polymer, and a dental adhesive primer, a dental adhesive bonding material, a dental adhesive composite resin, and a dental adhesive resin cement each using the dental adhesive composition.

23 Claims, No Drawings

(56) References Cited

U.S. PATENT DOCUMENTS

| | | | |
|---|---|---|---|
| 2007/0043142 A1 | 2/2007 | Dodiuk-Kenig et al. | |
| 2008/0139692 A1* | 6/2008 | Ishizu | C08F 8/04 522/173 |
| 2008/0207871 A1* | 8/2008 | Seiler | A61K 8/85 528/361 |
| 2009/0082528 A1 | 3/2009 | Basheer et al. | |
| 2010/0090157 A1* | 4/2010 | Rao | A61K 6/0023 252/79.1 |
| 2011/0045444 A1 | 2/2011 | Rao et al. | |
| 2011/0109076 A1* | 5/2011 | Grosset | C09D 11/102 283/57 |
| 2011/0135924 A1* | 6/2011 | Takahira | C08G 18/4202 428/355 R |
| 2012/0016050 A1* | 1/2012 | Leon | C08F 283/006 522/96 |
| 2012/0142805 A1* | 6/2012 | Grutzmacher | C08F 8/40 522/26 |
| 2012/0238662 A1* | 9/2012 | Klee | A61K 6/0038 523/116 |
| 2013/0324635 A1* | 12/2013 | Shimizu | C08G 83/005 522/173 |
| 2015/0190313 A1* | 7/2015 | Inaki | A61K 6/0023 523/118 |

FOREIGN PATENT DOCUMENTS

| | | | |
|---|---|---|---|
| JP | 2005-289860 A | 10/2005 | |
| JP | 2005289860 | * 10/2005 | ............ A61K 6/087 |
| JP | 2005289860 A | * 10/2005 | |
| JP | 2010-514782 A | 5/2010 | |
| WO | 0001108 A2 | 1/2000 | |
| WO | 0190968 A1 | 11/2001 | |
| WO | 03/013379 A2 | 2/2003 | |
| WO | WO 03013379 A2 | * 2/2003 | ........... A61K 6/0023 |
| WO | 2008/082929 A3 | 7/2008 | |
| WO | 2008082929 A2 | 7/2008 | |
| WO | WO 2008082929 A2 | * 7/2008 | ........... A61K 6/0023 |
| WO | 2009129359 A2 | 10/2009 | |
| WO | 2012/111550 A1 | 8/2012 | |

OTHER PUBLICATIONS

European Search Report for corresponding EP Patent Application No. 11839216.6-1853/2639998 PCT/CN2011076296; dated Sep. 1, 2017.

Decision to Grant a Patent for corresponding JP Application No. 2014-524731; dated Aug. 1, 2017.

P. Froehling., "Development of DSM's Hybrane Hyperbranched Polyesteramides," Journal of Polymer Science: Part A: Polymer Chemistry, vol. 42(13), pp. 3110-3115 (2004), Fig. 4.

* cited by examiner

DENTAL ADHESIVE COMPOSITION, DENTAL ADHESIVE PRIMER, DENTAL ADHESIVE BONDING MATERIAL, DENTAL ADHESIVECOMPOSITE RESIN, AND DENTAL ADHESIVE RESIN CEMENT

CROSS REFERENCE TO RELATED APPLICATIONS

This is the U.S. national stage of application No. PCT/JP2013/067682, filed on 27 Jun. 2013. Priority under 35 U.S.C. § 119(a) and 35 U.S.C. § 365(b) is claimed from Japanese Application No. 2012-154602, filed 10 Jul. 2012, the disclosure of which is also incorporated herein by reference.

TECHNICAL FIELD

The present invention relates to a dental adhesive composition, a dental adhesive primer, a dental adhesive bonding material, a dental adhesive composite resin, and a dental adhesive resin cement.

BACKGROUND ART

In a tooth damaged by caries or the like, when the damage is a relatively small cavity at an initial to middle stage, the cavity is often directly repaired with a composite resin in terms of esthetics, and the simplicity and rapidity of an operation. On the other hand, in the case of the repair of a relatively large cavity, the tooth is covered with a prosthesis made of a metal, a ceramic, or a dental resin via a resin cement. Various dental repairing materials to be used for various purposes such as the composite resin and the resin cement have been proposed (for example, Patent Literature 1).

A dental curable composition containing a radically polymerizable monomer such as a methacrylate-based polymerizable monomer as a main component is typically used as any such dental repairing material, e.g., the composite resin or the resin cement. In addition, the radically polymerizable monomer itself typically has no adhesive property to the tooth, and hence the dental curable composition containing the radically polymerizable monomer as a main component originally has a small adhesive force to the tooth. Accordingly, when the adhesive force between the dental curable composition and the tooth is weak, it becomes difficult to maintain the state of adhesion between the dental curable composition and the tooth owing to a polymerization shrinkage stress caused at the time of its curing.

Meanwhile, the hard tissue of the tooth is formed of enamel and dentin, and hence adhesive properties to both the enamel and the dentin are clinically required. Accordingly, the following method has heretofore been employed. The dental curable composition containing the radically polymerizable monomer as a main component is bonded to the tooth via a bonding material, and the surface of a tooth is pretreated prior to the application of the bonding material in order that the adhesive property of the bonding material to the tooth may be improved. A pretreating material to be used in such pretreatment of the tooth is generally an acid aqueous solution that decalcifies the surface of the tooth, and an aqueous solution of an acid such as phosphoric acid has been used. The mechanism via which the bonding material is bonded to the pretreated surface is said to be: such macroscopic mechanical fitting that the bonding material penetrates a surface roughened by etching with the acid aqueous solution and then cures in (1) the case where the hard tissue of the tooth is the enamel; or such microscopic mechanical fitting that the bonding material penetrates a fine void of a spongy collagen fiber exposed to the surface of the tooth after the decalcification and then cures in (2) the case where the hard tissue of the tooth is the dentin.

However, the penetration of the bonding material into the collagen fiber is not as easy as the penetration of the bonding material into the surface of the enamel. Accordingly, in consideration of the securement of adhesive property not only to the enamel but also to the dentin, etching treatment involving using the acid aqueous solution and primer treatment involving using a penetration enhancer called a primer are generally performed in the stated order prior to the use of the bonding material. That is, an operation in the case where the dental curable composition containing the radically polymerizable monomer as a main component is used has been a three-step system requiring two-stage pretreatment before the application of the bonding material for obtaining good adhesive strengths to both the enamel and the dentin. Accordingly, a problem in that the operation is complicated has arisen.

In view of the foregoing, in recent years, the following two-step system has been proposed for simplifying the operation of clinical therapy (see Patent Literature 2). Treatment involving using a self-etching primer that performs such etching treatment and primer treatment as described above at the same time, and treatment for applying the bonding material are performed in the stated order, and then the dental curable composition is bonded to the tooth. The following one-step system has also been proposed (self-bonding treatment, see Patent Literature 3). After treatment for applying a bonding material (self-etching bonding material) that does not require pretreatment such as the etching treatment or the primer treatment, the dental curable composition is bonded to the tooth.

Further, studies have been made on the following self-adhesive composite resin or self-adhesive resin cement. Even when a cavity is filled with the composite resin or the tooth is covered with a prosthesis via the resin cement, the composite resin or the resin cement does not require pretreatment such as the etching treatment or the primer treatment and treatment for applying the bonding material, and is directly bonded to the tooth. It should be noted that each of the related-art dental adhesive compositions such as the self-etching primer, the self-etching bonding material, the self-adhesive composite resin, and the self-adhesive resin cement contains an acidic group-containing polymerizable monomer as a main component, and has a self-etching function and adhesive property.

CITATION LIST

Patent Literature

[PTL 1] JP 2010-514782 A
[PTL 2] JP 06-009327 A
[PTL 3] JP 2000-159621 A

SUMMARY OF INVENTION

Technical Problem

However, the related-art dental adhesive composition given in Patent Literature 2 or 3 never has a satisfactory adhesive strength owing to an influence of a polymerization shrinkage stress caused upon curing of a polymerizable monomer, though some degree of adhesive strength-improving effect can be confirmed. In this case, a gap may be formed between the adhesive surfaces of the cured dental curable composition such as a composite resin or a resin cement and the tooth. When such gap occurs, plaque is liable to accumulate in the gap and hence secondary caries is liable to occur. In addition, the cured composite resin or resin cement is liable to fall from the adhesive surface of the tooth.

In this kind of situation, a dental adhesive composition into which a polymerizable monomer that additionally improves adhesive property to the tooth has been incorporated has been developed for obtaining an additionally high adhesive strength. For example, a method involving using not only a polymerizable monomer that has heretofore been used but also a radically polymerizable monomer having a large molecular weight, or a method in which a cationically polymerizable monomer that undergoes smaller polymerization shrinkage than that of radical polymerization is used, and the polymerizable monomer is polymerized and cured by cationic ring-opening polymerization has been proposed for suppressing polymerization shrinkage at the time of the curing of the dental adhesive composition. However, a suppressing effect exhibited by each of the methods is limited, and hence it has been unable to secure a sufficient adhesive force and sufficient adhesion durability. Accordingly, a dental adhesive composition having a sufficient adhesive force and sufficient adhesion durability has been required.

The present invention has been made in view of the above-mentioned circumstances, and an object of the present invention is to provide a dental adhesive composition, a dental adhesive primer, a dental adhesive bonding material, a dental adhesive composite resin, and a dental adhesive resin cement each having an excellent adhesive force and excellent adhesion durability.

Solution to Problem

The above-mentioned object is achieved by the present invention described below. That is, a dental adhesive composition of the present invention includes: (A) a polymerizable monomer containing an acidic group-containing polymerizable monomer; and (B) a dendritic polymer.

In a dental adhesive composition according to one embodiment of the present invention, it is preferred that the acidic group include a phosphate group.

In a dental adhesive composition according to another embodiment of the present invention, it is preferred that (B) the dendritic polymer include at least one kind of material selected from a dendrimer and a hyperbranched polymer, and have a weight-average molecular weight of 1,500 or more.

In a dental adhesive composition according to another embodiment of the present invention, it is preferred that (B) the dendritic polymer have a network structure including at least one kind of branching portion selected from a trifurcated branching portion and a four-furcated branching portion, and a connecting portion for connecting the branching portions.

In a dental adhesive composition according to another embodiment of the present invention, it is preferred that (B) the dendritic polymer include a hyperbranched polymer containing a unit structure represented by the following general formula (I), and at least one unit structure selected from a unit structure represented by the following general formula (IIA) and a unit structure represented by the following general formula (IIB):

[Chem. 1]

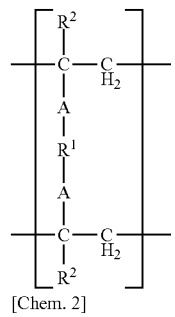

General formula (I)

[Chem. 2]

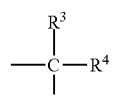

General formula (IIA)

[Chem. 3]

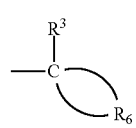

General formula (IIB)

in the general formula (I), A represents a single bond for bonding C and $R^1$, >C=O, —O—, —COO—, or —COO—$CH_2$—, $R^1$ represents a divalent saturated aliphatic hydrocarbon group or a divalent aromatic hydrocarbon group, and $R^2$ represents a hydrogen atom or a methyl group, in the general formula (IIA) and the general formula (IIB), $R^3$, $R^4$, and $R^5$ each represent a hydrogen atom, an alkyl group having a main chain containing 1 to 5 carbon atoms, an alkoxycarbonyl group having a main chain containing 1 to 5 carbon atoms, an aryl group, or a cyano group, and in the general formula (IIB), $R^6$ represents an alkylene group having a main chain containing 4 to 10 carbon atoms.

It is preferred that a dental adhesive composition according to another embodiment of the present invention further include (C) water.

It is preferred that a dental adhesive composition according to another embodiment of the present invention further include (D) a polymerization initiator.

It is preferred that a dental adhesive composition according to another embodiment of the present invention further include (E) a filler.

A dental adhesive primer of the present invention includes: (A) a polymerizable monomer containing an acidic group-containing polymerizable monomer; (B) a dendritic polymer; and (C) water.

A dental adhesive bonding material of the present invention includes: (A) a polymerizable monomer containing an acidic group-containing polymerizable monomer; (B) a dendritic polymer; (C) water; and (D) a polymerization initiator.

A dental adhesive composite resin of the present invention includes: (A) a polymerizable monomer containing an acidic group-containing polymerizable monomer; (B) a dendritic polymer; (D1) a photopolymerization initiator; and (E) a filler.

A dental adhesive resin cement of the present invention includes: (A) a polymerizable monomer containing an acidic group-containing polymerizable monomer; (B) a dendritic polymer; (D2) a chemical polymerization initiator; and (E) a filler.

Advantageous Effects of Invention

According to embodiments of the present invention, it is possible to provide the dental adhesive composition, the dental adhesive primer, the dental adhesive bonding material, the dental adhesive composite resin, and the dental adhesive resin cement each having an excellent adhesive force and excellent adhesion durability.

DESCRIPTION OF EMBODIMENTS

Hereinafter, a dental adhesive composition according to a preferred embodiment of the present invention is described. However, the present invention is by no means limited to an embodiment to be described below.

The dental adhesive composition according to this embodiment includes: (A) a polymerizable monomer containing an acidic group-containing polymerizable monomer; and (B) a dendritic polymer. The adhesive force of the dental adhesive composition according to this embodiment to a bonding object and its adhesion durability can be improved by blending a combination of the polymerizable monomer containing the acidic group-containing polymerizable monomer and the dendritic polymer. This is probably because when the dendritic polymer is used, large polymerization shrinkage involved in the polymerization of the polymerizable monomer containing the acidic group-containing polymerizable monomer hardly occurs and hence the polymerization shrinkage stress of the polymerizable monomer containing the acidic group-containing polymerizable monomer is suppressed. Accordingly, a reduction in adhesive force of the polymerizable monomer containing the acidic group-containing polymerizable monomer to the bonding object due to the polymerization shrinkage stress caused upon curing of the polymerizable monomer containing the acidic group-containing polymerizable monomer at an interface with the bonding object can be suppressed. As a result, the polymerizable monomer containing the acidic group-containing polymerizable monomer can exhibit its original adhesive force to the bonding object. Here, (B) the dendritic polymer refers to a tree-shaped multibranched polymer that is formed of many branches and is entirely not of a string-like shape but of a shape close to a spherical shape.

Next, details about (A) the polymerizable monomer containing the acidic group-containing polymerizable monomer and (B) dendritic polymer in the dental adhesive composition according to this embodiment are described.

(A) Polymerizable Monomer Containing Acidic Group-Containing Polymerizable Monomer Although (A) the polymerizable monomer containing the acidic group-containing polymerizable monomer in the dental adhesive composition according to this embodiment may be formed only of the acidic group-containing polymerizable monomer, the polymerizable monomer suitably further contains a polymerizable monomer free of any acidic group from the viewpoint of regulating the strength of a cured body and the penetrability of the dental adhesive composition into the bonding object in order that an additionally excellent adhesive strength to the bonding object may be obtained.

In addition, from the viewpoints of adhesive strengths to both enamel and dentin, the blending amount of the acidic group-containing polymerizable monomer falls within preferably the range of from 3 parts by mass to 70 parts by mass, more preferably the range of from 5 parts by mass to 60 parts by mass, most preferably the range of from 10 parts by mass to 55 parts by mass with respect to 100 parts by mass of the total amount of (A) the polymerizable monomer containing the acidic group-containing polymerizable monomer and (B) the dendritic polymer. Setting the blending amount of the acidic group-containing polymerizable monomer to 3 parts by mass or more facilitates the securement of a sufficient adhesive force to the enamel. In addition, setting the blending amount of the acidic group-containing polymerizable monomer to 70 parts by mass or less facilitates the prevention of a reduction in adhesive force of the composition to the dentin.

Here, the acidic group-containing polymerizable monomer is not particularly limited as long as the polymerizable monomer has at least one polymerizable unsaturated group and at least one acidic group in one molecule, and a known compound may be used. Here, examples of the polymerizable unsaturated group include: a (meth)acryloyl group and derivative groups of a (meth)acryloyl group such as a (meth)acryloyloxy group, a (meth)acryloylamino group, and a (meth)acryloylthio group; a vinyl group; an aryl group; a styryl group; and a (meth)acrylamide group.

In addition, the term "acidic group" as used in the description of the present application means not only (1) a free acidic group having —OH such as a phosphinico group $\{=P(=O)OH\}$, a phosphono group $\{-P(=O)(OH)_2\}$, a carboxyl group $\{-C(=O)OH\}$, or a sulfo group ($-SO_3H$) but also such a group that an aqueous solution or aqueous suspension of a polymerizable monomer having the group shows acidity like (2) an acid anhydride structure obtained by the dehydration condensation of two of the acidic groups each having —OH given in the item (1) (such as —C(=O)—O—C(=O)—), (3) an acid halide group obtained by substituting-OH of an acidic group having —OH given in the item (1) with a halogen (such as —C(=O)Cl), or the like. The pKa of the acidic group is preferably less than 5.

Specific examples of the acidic group-containing polymerizable monomer include acidic group-containing polymerizable monomers each having a phosphinicooxy group or a phosphonooxy group in the molecule (hereinafter sometimes referred to as "polymerizable acidic phosphate") such as 2-(meth)acryloyloxyethyl dihydrogen phosphate, bis(2-(meth)acryloyloxyethyl) hydrogen phosphate, 2-(meth)acryloyloxyethyl phenyl hydrogen phosphate, 10-(meth)acryloyloxydecyl dihydrogen phosphate, 6-(meth)acryloyloxyhexyl dihydrogen phosphate, bis(6-(meth)acryloyloxyhexyl) hydrogen phosphate, and 2-(meth)acryloyloxyethyl 2-bromoethyl hydrogen phosphate, and acid anhydrides and acid halides thereof. Further examples of the acidic group-containing polymerizable monomer include acidic group-containing polymerizable monomers each having one carboxyl group in the molecule such as (meth)acrylic acid, N-(meth)acryloylglycine, N-(meth)acryloylaspartic acid, N-(meth)acryloyl-5-aminosalicylic acid, 2-(meth)acryloyloxyethyl hydrogen succinate, 2-(meth)acryloyloxyethyl hydrogen phthalate, 2-(meth)acryloyloxyethyl hydrogen malate, 6-(meth)acryloyloxyethylnaphthalene-1,2,6-tricarboxylic acid, O-(meth)acryloyltyrosine, N-(meth)acryloyltyrosine, N-(meth)acryloylphenylalanine, N-(meth)acryloyl-p-aminobenzoic acid, N-(meth)acryloyl-O-aminobenzoic acid, p-vinylbenzoic acid, 2-(meth)acryloyloxybenzoicacid, 3-(meth)acryloyloxybenzoicacid, 4-(meth)acryloyloxybenzoic acid, N-(meth)acryloyl-5- aminosalicylic acid, and N-(meth)acryloyl-4-aminosalicylic acid, and acid anhydrides and acid halides thereof.

Further examples of the acidic group-containing polymerizable monomer include acidic group-containing polymerizable monomers each having a plurality of carboxyl groups or acid anhydride groups thereof in the molecule such as 11-(meth)acryloyloxyundecane-1,1-dicarboxylic acid, 10-(meth)acryloyloxydecane-1,1-dicarboxylic acid, 12-(meth)acryloyloxydodecane-1,1-dicarboxylic acid, 6-(meth)acryloyloxyhexane-1,1-dicarboxylic acid, 2-(meth)acryloyloxyethyl-3'-methacryloyloxy-2'-(3,4-dicarboxybenzoyloxy)propyl succinate, 1,4-bis(2-(meth)acryloyloxyethyl) pyromellitate, N,0-di(meth)acryloyltyrosine, 4-(2-(meth)acryloyloxyethyl) trimellitate, 4-(meth)acryloyloxyethyl trimellitate, 4-(meth)acryloyloxybutyl trimellitate, 4-(meth)acryloyloxyhexyl trimellitate, 4-(meth)acryloyloxydecyl trimellitate, 4-acryloyloxybutyl trimellitate, 6-(meth)acryloyloxyethylnaphthalene-1,2,6-tricarboxylic anhydride, 6-(meth)acryloyloxyethylnaphthalene-2,3,6-tricarboxylic anhydride, 4-(meth)acryloyloxyethylcarbonylpropionoyl-1,8-naphthalic anhydride, and 4-(meth)acryloyloxyethylnaphthalene-1,8-tricarboxylic anhydride, and acid anhydrides and acid halides thereof.

Further examples of the acidic group-containing polymerizable monomer include acidic group-containing polymerizable monomers each having a phosphono group in the molecule such as vinylphosphonic acid and p-vinylbenzenephosphonic acid.

Further examples of the acidic group-containing polymerizable monomer include acidic group-containing polymerizable monomers each having a sulfo group in the molecule such as 2-(meth)acrylamido-2-methylpropanesulfonic acid, p-vinylbenzenesulfonic acid, and vinylsulfonic acid.

Further, in addition to the examples given above, there may also be suitably used an acidic group-containing polymerizable monomer described as a component of a dental adhesive material, which is disclosed in, for example, JP 54-11149 A, JP 58-140046 A, JP 59-15468 A, JP 58-173175 A, JP 61-293951 A, JP 07-179401 A, JP 08-208760 A, JP 08-319209 A, JP 10-236912 A, or JP 10-245525 A.

One kind of those acidic group-containing polymerizable monomers may be used alone, or a plurality of kinds thereof may be used in combination.

Of the acidic group-containing polymerizable monomers, an acidic group-containing polymerizable monomer whose acidic group is a phosphate group is preferred because of its excellent adhesive property to the bonding object. Such acidic group-containing polymerizable monomer having a phosphate group is particularly preferably a polymerizable acidic phosphate having a phosphoric acid dihydrogen monoester group {—O—P(=O) (OH)$_2$} or a phosphoric acid hydrogen diester group {(—O—)$_2$P(=O)OH}. In addition, when the dental adhesive composition according to this embodiment is a photocurable adhesive composition that cures through photoirradiation, the polymerizable unsaturated group constituting the acidic group-containing polymerizable monomer is preferably a derivative group of a (meth)acryloyl group because of its good polymerizability at the time of the photoirradiation.

On the other hand, when a polymerizable monomer except the acidic group-containing polymerizable monomer (hereinafter sometimes abbreviated as "other polymerizable monomer") is used in (A) the polymerizable monomer containing the acidic group-containing polymerizable monomer, a known radically polymerizable monomer is used as the other polymerizable monomer without any limitation as long as the monomer is free of any acidic group and has a polymerizable unsaturated group. In general, a (meth)acrylate-based polymerizable monomer is suitably used from the viewpoints of a curing rate and the mechanical properties of the cured body. Specific examples thereof include monomers described in the following sections (I) to (III).

(I) Bifunctional Radically Polymerizable Monomer

A bifunctional radically polymerizable monomer is exemplified by the following items (i) and (ii).

(i) Aromatic Compound-Based Bifunctional Radically Polymerizable Monomer

As an aromatic compound-based bifunctional radically polymerizable monomer, there are given: 2,2-bis(methacryloyloxyphenyl)propane, 2,2-bis[4-(3-methacryloyloxy)-2-hydroxypropoxyphenyl]propane (hereinafter abbreviated as bis-GMA), 2,2-bis(4-methacryloyloxyphenyl)propane, 2,2-bis(4-methacryloyloxypolyethoxyphenyl)propane (hereinafter abbreviated as D-2.6E), 2,2-bis(4-methacryloyloxydiethoxyphenyl)propane, 2,2-bis(4-methacryloyloxytetraethoxyphenyl)propane, 2,2-bis(4-methacryloyloxypentaethoxyphenyl)propane, 2,2-bis(4-methacryloyloxydipropoxyphenyl)propane, 2(4-methacryloyloxydiethoxyphenyl)-2(4-methacryloyloxytriethoxyphenyl)propane, 2(4-methacryloyloxydipropoxyphenyl)-2-(4-methacryloyloxytriethoxyphenyl)propane, 2,2-bis(4-methacryloyloxypropoxyphenyl)propane, and 2,2-bis(4-methacryloyloxyisopropoxyphenyl)propane, and acrylates corresponding to these methacrylates; diadducts each obtained by addition of a vinyl monomer having an —OH group, like a methacrylate such as 2-hydroxyethyl methacrylate, 2-hydroxypropylmethacrylate, or 3-chloro-2-hydroxypropyl methacrylate, or an acrylate corresponding to each of these methacrylates and a diisocyanate compound having an aromatic group, such as diisocyanatomethylbenzene or 4,4'-diphenylmethane diisocyanate; and the like.

(ii) Aliphatic Compound-Based Bifunctional Radically Polymerizable Monomer

As an aliphatic compound-based bifunctional radically polymerizable monomer, there are given: ethylene glycol dimethacrylate, diethylene glycol dimethacrylate, triethylene glycol dimethacrylate (hereinafter abbreviated as 3G), tetraethylene glycol dimethacrylate, neopentyl glycol dimethacrylate, 1,3-butanediol dimethacrylate, 1,4-butanediol dimethacrylate, 1,6-hexanediol dimethacrylate (hereinafter abbreviated as HD), 1,9-nonanediol dimethacrylate (hereinafter abbreviated as ND), and acrylates corresponding to these methacrylates; diadducts each obtained from an adduct of a vinyl monomer having an —OH group, like a methacrylate such as 2-hydroxyethyl methacrylate, 2-hydroxypropyl methacrylate, or 3-chloro-2-hydroxypropyl methacrylate, or an acrylate corresponding to each of these methacrylates and a diisocyanate compound, such as hexamethylene diisocyanate, trimethylhexamethylene diisocyanate, diisocyanatomethylcyclohexane, isophorone diisocyanate, or methylenebis(4-cyclohexyl isocyanate); 1,2-bis(3-methacryloyloxy-2-hydroxypropoxy)ethyl; and the like.

(II) Trifunctional Radically Polymerizable Monomer

As a trifunctional radically polymerizable monomer, there are given methacrylates, acrylates corresponding to the methacrylates, and the like, the metacrylates including trimethylolpropane trimethacrylate, trimethylolethane trimethacrylate, pentaerythritol trimethacrylate, and trimethylolmethane trimethacrylate.

(III) Tetrafunctional Radically Polymerizable Monomer

As a tetrafunctional radically polymerizable monomer, there are given pentaerythritol tetramethacrylate, pentaerythritol tetraacrylate, diadducts each obtained from an adduct of a diisocyanate compound and glycidol dimethacrylate, and the like, the diisocyanate compound being, for example, diisocyanatomethylbenzene, diisocyanatomethylcyclohexane, isophorone diisocyanate, hexamethylene diisocyanate, trimethylhexamethylene diisocyanate, methylenebis(4-cyclohexyl isocyanate), 4,4-diphenylmethane diisocyanate, or tolylene-2,4-diisocyanate.

A plurality of kinds of these polyfunctional (meth)acrylate-based radically polymerizable monomers may be used in combination as required.

Further, as required, there may be used monofunctional (meth)acrylate-based monomers including methacrylates such as methyl methacrylate, ethyl methacrylate, isopropyl methacrylate, hydroxyethyl methacrylate, tetrahydrofurfuryl methacrylate, and glycidyl methacrylate, and acrylates corresponding to these methacrylates, and radically polymerizable monomers other than the (meth)acrylate-based monomers.

(B) Dendritic Polymer

While a conventional polymer is generally of a string-like (or linear) shape, (B) the dendritic polymer to be used in the dental adhesive composition according to this embodiment is a highly branched polymer in which a branched structure is three-dimensionally repeated. Accordingly, the dendritic polymer has, for example, the following characteristics: (1) the polymer has a shape close to a spherical shape; (2) the polymer has a size of nanometer order; (3) the degree of entanglement between its molecules is low and hence the polymer shows behavior like a fine particle; (4) the polymer has higher dispersibility upon its mixing with a solvent or a liquid polymerizable monomer than a string-like polymer does and an increase in viscosity of the mixture can be suppressed to a low level as compared with the string-like polymer; (5) the surface of the polymer has many molecular chain terminals into which groups each having functionality can be introduced; and (6) the polymer has a void in the molecule. Accordingly, the dendritic polymer can be finely dispersed even in a liquid or paste-like composition to be generally used as a dental material without involving a remarkable increase in viscosity of the composition. In addition, the dendritic polymer has a high affinity for a polymerizable monomer. As a result, when the dendritic polymer is blended in a certain amount into the dental adhesive composition, the effect by which the amount of a polymerizable monomer in the entirety of the composition is substantially reduced and the effect by which the polymer is compatible with the cured body of the polymerizable monomer can be coupled with each other to reduce polymerization shrinkage at the time of the curing, and hence high adhesive property to a tooth is exhibited.

Examples of the dendritic polymer include a dendrimer, a linear dendritic polymer, a dendrigraft polymer, a hyperbranched polymer, a star-hyperbranched polymer, and a hypergraft polymer. Of those, each of the former three kinds has a degree of branching of 1 and has a structure free of any defect. In contrast, each of the latter three kinds has a random branched structure that may contain a defect.

The branched structure of the dendrimer is formed by subjecting a monomer having many functional groups to a chemical reaction stage by stage. Examples of a method of synthesizing the dendrimer may include a divergent method in which the dendrimer is synthesized from its center to the outside and a convergent method in which the dendrimer is synthesized from the outside to the center. Examples of the dendrimer include an amidoamine-based dendrimer (U.S. Pat. No. 4,507,466 A and the like) and a phenyl ether-based dendrimer (U.S. Pat. No. 5,041,516 A and the like). With regard to the amidoamine-based dendrimer, a dendrimer having a terminal amino group and a carboxylic acid methyl ester group is commercially available from Aldrich as a "Starburst™ (PAMAM)." Amidoamine-based dendrimers having corresponding terminals synthesized by causing the terminal amino group of the amidoamine-based dendrimer to react with various acrylic acid derivatives and methacrylic acid derivatives may also be used.

In addition, with regard to the phenyl ether-based dendrimer, various kinds thereof have been described in the Journal of American Chemical Society, Vol. 112 (1990, p. 7638 to 7647). Compounds obtained by substituting a terminal benzyl ether bond as a terminal of the phenyl ether-based dendrimer with groups having various chemical structures may also be used.

The hyperbranched polymer is a synthetic polymer generally obtained by a one-stage polymerization method unlike the dendrimer whose branched structure is formed by precisely controlling a multi-stage synthesis reaction. The hyperbranched polymer has a molecular weight distribution and an insufficiently branched unit because a large molecule is synthesized in one stage. However, the hyperbranched polymer has the following great merits: the hyperbranched polymer can be easily produced and its production cost is low as compared with the dendrimer.

In addition, when the conditions under which the hyperbranched polymer is synthesized are appropriately selected, its degree of branching can be controlled and hence molecular design in accordance with an application can be performed. The hyperbranched polymer is synthesized by using a monomer, which has, in one molecule, two or more first reaction points corresponding to branching portions and only one second reaction point corresponding to a connecting portion and different in kind from the first reaction points, through a one-stage synthesis process (Macromolecules, Vol. 29 (1996), p. 3831 to 3838).

For example, a self-condensation method for an ABx-type monomer having two kinds of functional groups in one molecule or a method involving subjecting an A2-type monomer and a B3-type monomer to polycondensation has been known as such synthesis process (Dendritic Polymer-World of High Functionality expanded by Multibranched Structure, NTS Inc. (2005)). In addition, a branched structure is formed in one stroke by any such method. It should be noted that the capital alphabet letters "A" and "B" in the description of the synthesis methods described above represent functional groups different from each other, and Arabic numerals represented in combination with the "A" and "B" each represent the number of functional groups in one molecule.

In addition, a self-condensing vinyl polymerization method (SCVP method) has been known as a method involving polymerizing a compound having, in one molecule, a functional group capable of initiating polymerization and a vinyl group to provide a hyperbranched polymer (Science, 269, 1080 (1995)). In addition, an initiator-fragment incorporation radical polymerization method (IFIRP) has been known as a method involving polymerizing a molecule having a plurality of polymerizable groups with a large amount of an initiator to synthesize such a hyperbranched polymer that an initiator fragment is taken in a produced polymer (J. Polymer. Sci.: Part A: Polym. Chem., 42, 3038 (2003)).

The hyperbranched polymer can take various structures depending on the ABx-type monomer to be used and the chemical modification of a surface functional group of the resultant polymer. From the viewpoint of classification of skeleton structures, examples of the hyperbranched polymer include hyperbranched polycarbonate, hyperbranched polyether, hyperbranched polyester, hyperbranched polyphenylene, hyperbranched polyamide, hyperbranched polyimide, hyperbranched polyamide imide, hyperbranched polysiloxane, and hyperbranched polycarbosilane. In addition, as a terminal group of any one of those hyperbranched polymers, there are given, for example, an alkyl group, a phenyl group, a heterocyclic group, a (meth)acrylic group, an allyl group, a styryl group, a hydroxyl group, an amino group, an imino group, a carboxyl group, a halogeno group, an epoxy group, a thiol group, and a silyl group. In addition, the surface of the hyperbranched polymer may be provided with a functional group in accordance with a purpose by further chemically modifying any such terminal group.

In the dental adhesive composition according to this embodiment, only one kind of those dendritic polymers may be used alone, or two or more kinds of the dendritic polymers may be used in combination. Of the dendritic polymers listed above, a dendrimer or a hyperbranched polymer may be particularly suitably used.

The dendritic polymer can be finely dispersed in the dental adhesive composition into which the dendritic polymer is blended with a high affinity without increasing the viscosity of the composition because the degree of entanglement between its molecules is low and hence the dendritic polymer shows behavior like a fine particle. Accordingly, when the dendritic polymer is blended in a certain amount into the dental adhesive composition, polymerization shrinkage at the time of its curing can be significantly reduced. As a result, the adhesive force and adhesion durability of the dental adhesive composition according to this embodiment can be improved. In addition, the molecular weight of the dendritic polymer is not particularly limited but its weight-average molecular weight measured by a gel permeation chromatography (GPC) method is preferably 1,500 or more, more preferably 10,000 or more, most preferably 15,000 or more. In addition, an upper limit for the weight-average molecular weight is not particularly limited, but in the case where the weight-average molecular weight is excessively large, the handleability and adhesive property of the dental adhesive composition may be liable to change largely when the blending amount of the dendritic polymer is largely changed. Accordingly, the weight-average molecular weight is preferably 200,000 or less, more preferably 100,000 or less, most preferably 80,000 or less in practical use.

The blending amount of the dendritic polymer to be incorporated into the dental adhesive composition, which is not particularly limited, falls within preferably the range of from 5 parts by mass to 40 parts by mass, more preferably the range of from 7 parts by mass to 35 parts by mass, most preferably the range of from 10 parts by mass to 30 parts by mass with respect to 100 parts by mass of the total amount of (A) the polymerizable monomer containing the acidic group-containing polymerizable monomer and (B) the dendritic polymer. Setting the blending amount of the dendritic polymer to 5 parts by mass or more facilitates an additional reduction in polymerization shrinkage ratio upon curing of the dental adhesive composition. In addition, setting the blending amount of the dendritic polymer to 40 parts by mass or less prevents the deterioration of the handleability, and if needed, facilitates the securement of the mechanical strength of the dental adhesive composition.

Although any one of the various dendritic polymers described above may be utilized as the dendritic polymer to be used in the dental adhesive composition according to this embodiment, the dendritic polymer preferably has a network structure (network multibranched structure) including at least one kind of branching portion selected from a trifurcated branching portion and a four-furcated branching portion, and a connecting portion for connecting the branching portions. The dendritic polymer having such network structure is typically, for example, the hyperbranched polymer. It should be noted that as branches in the network structure are formed in a more developed manner, the movement of each of the molecular chains constituting the network structure is restricted and entanglement between the molecular chains is suppressed, and hence even when the ratio at which the dendritic polymer is blended into the dental adhesive composition is increased, it becomes easier to suppress an increase in its viscosity.

In addition, a terminal portion of the network structure may have a group having a reactive unsaturated bond, or a reactive functional group such as a hydrosilyl group or an epoxy group, or may be substantially free of any reactive functional group. It should be noted that when the terminal portion of the network structure is substantially free of any reactive functional group, the portion is occupied by a nonreactive functional group such as an alkyl group. Here, the phrase "substantially free of any reactive functional group" means not only the case where the terminal portion of the network structure has no reactive functional group but also the case where a reactive functional group resulting from, for example, a side reaction at the time of the synthesis of the dendritic polymer having the network structure or an impurity in a reaction system is introduced, albeit in a slight amount, into the terminal portion of the network structure.

In the case where the terminal portion of the network structure has a reactive functional group, particularly when the reactive functional group is a group having a reactive unsaturated bond, the formation of a bond between the molecules of the dendritic polymer or between the dendritic polymer and a polymerizable monomer facilitates an additional increase in mechanical strength of a cured product of the dental adhesive composition.

On the other hand, in the case where a reactive functional group remains in the cured product after the curing of the dental adhesive composition, when the cured product is exposed to food and drink in an intraoral environment, or is exposed to natural light or indoor light, the reactive functional group remaining in the cured product reacts with the food and drink, the natural light, or the indoor light, and hence the cured product is liable to color or discolor. However, when the terminal portion of the network structure is substantially free of any reactive functional group, it is extremely easy to suppress the occurrence of such coloring or discoloring of the cured product.

It should be noted that the internal portion of the network structure may also have a reactive functional group. However, the reactive functional group positioned in the internal portion of the network structure hardly contributes to an increase in mechanical strength of the cured product because the group hardly reacts with any other dendritic polymer or a polymerizable monomer as compared with the reactive functional group positioned in the terminal portion. Meanwhile, the reactive functional group positioned in the internal portion of the network structure has a high risk of causing the coloring or the discoloring as in the reactive functional group positioned in the terminal portion. In consideration of the foregoing, it is preferred that the internal portion of the network structure be substantially free of any reactive functional group.

The number of branches of a branching portion in the network structure constituting the hyperbranched polymer is generally 3 or 4. A trifurcated branching portion (three-branching portion) is preferably formed of a nitrogen atom, a trivalent cyclic hydrocarbon group, or a trivalent heterocyclic group, and a four-furcated branching portion (four-branching portion) is preferably formed of a carbon atom, a silicon atom, a tetravalent cyclic hydrocarbon group, or a tetravalent heterocyclic group. It should be noted that the (trivalent or tetravalent) cyclic hydrocarbon groups are roughly classified into, for example, an aromatic hydrocarbon group such as a (trivalent or tetravalent) benzene ring and an alicyclic hydrocarbon group such as a (trivalent or tetravalent) cyclohexane ring. In addition, a known heterocyclic group may be utilized as the (trivalent or tetravalent) heterocyclic group. It should be noted that a group represented by the following structural formula 1 may be given as an example of the trivalent heterocyclic group.

[Chem. 4]

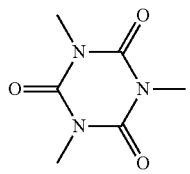

Structural formula 1

In addition, a connecting portion connecting branching portions is preferably one kind of divalent group or atom selected from the following structural formula group X. Here, in the structural formula group X, $R^{11}$ represents an aromatic hydrocarbon group, or an alkylene group having 40 or less carbon atoms, and n represents an integer selected from the range of from 1 to 9. It should be noted that two or more of a plurality of connecting portions bonded to one branching portion may be identical to each other, or all connecting portions bonded to one branching portion may be different from each other.

[Chem. 5]

—$R^{11}$—  —O—  —O—$R^{11}$—

—O—$R^{11}$—O—  —(C=O)—

—(C=O)O—  —(C=O)O—$R^{11}$—

—$R^{11}$(C=O)O—  —$R^{11}$—O(C=O)—$R^{11}$—

—NH—$R^{11}$—  —NH—  —NH(C=O)O—

—NH(C=O)—

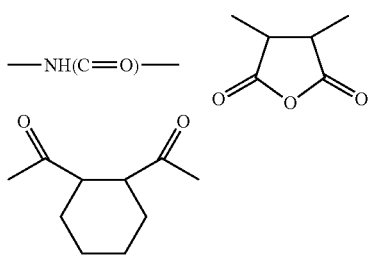

Structural Formula Group X

[Chem. 6]

—$R^{11}$—O—$R^{11}$—   —(C=O)—O—$R^{11}$—O—

—(C=O)NH—$R^{11}$—   —NH(C=O)—$R^{11}$—

—$R^{11}$—(C=O)NH—$R^{11}$—

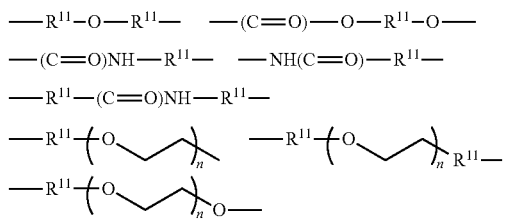

Structural Formula Group X

In addition, general examples of such terminal portion of the network structure include a hydrogen atom, a halogen atom (—F, —Cl, —Br, or —I), a styryl group, an epoxy group, a glycidyl group, one kind of monovalent group selected from the following structural formula group Z, a monovalent group represented by the general formula (IIA) to be described later, a monovalent group represented by the general formula (IIB) to be described later, a monovalent cyclic hydrocarbon group, and a monovalent heterocyclic group. Here, a group excluding a hydrogen atom and a halogen atom out of the terminal portions may be further chemically modified. In addition, hydrogen atoms bonded to the rings of the monovalent cyclic hydrocarbon group and the monovalent heterocyclic group may each be substituted with a halogen atom, a carboxyl group, an amino group, a hydroxyl group, or a monovalent carboxylate. In addition, the monovalent cyclic hydrocarbon groups are roughly classified into, for example, an aromatic hydrocarbon group such as a monovalent benzene ring and an alicyclic hydrocarbon group such as a monovalent cyclohexane ring.

—$R^{12}$—$NH_2$

—O(C=O)CH=$CH_2$  =O(C=O)C($CH_3$)=$CH_2$

—OH  —$R^{13}$—OH

—$R^{13}$—O—$R^{12}$  —$R^{13}$—(C=O)OH

—$R^{13}$—(C=O)$OCH_3$

—O(C=O)CH=CH(C=O)OH

—(C=O)OH  —(C=O)$R^{12}$

—(C=O)$OR^{12}$  =(C=O)OSi($CH_3$)$_3$

—(C=O)NH—$R^{12}$  —NH(C=O)$R^{12}$

—$NH_3Cl$  —$NH_3Br$

SiH($CH_3$)$_2$  —Si($CH_3$)$_3$

—CN  —O(P=O)(OH)$_2$

—(P=O)(OH)$_2$  —S—(C=S)—N($C_2H_5$)$_2$  [Chem. 7]

Structural Formula Group Z

It should be noted that in the structural formula group Z, $R^{12}$ represents a monovalent aromatic hydrocarbon group or an alkyl group having 40 or less carbon atoms, and $R^{13}$ represents a divalent aromatic hydrocarbon group or an alkylene group having 40 or less carbon atoms. In addition, when a group represented in the structural formula group Z contains both $R^{12}$ and $R^{13}$, the structures of both the groups may be identical to or different from each other except a valence.

The dendritic polymer that may be suitably used in the dental adhesive composition according to this embodiment is specifically, for example, a dendritic polymer having a network structure formed by the bonding of unit structures each represented by the following general formula (i).

[Chem. 8]

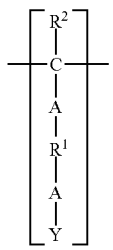

General formula (i)

Here, in the general formula (i), A represents a single bond for bonding C and R¹ (i.e., a state where C and R¹ are merely bonded to each other via a σ bond), >C═O, —O—, —COO—, or —COO—CH₂—, R¹ represents a divalent saturated aliphatic hydrocarbon group or a divalent aromatic hydrocarbon group, R² represents a hydrogen atom or a methyl group, and Y represents a group represented by the following general formula (iia) or a group represented by the following general formula (iib). When the network structure excluding the terminal portion is constituted of a unit structure represented by the general formula (i), the unit structure represented by the general formula (i) constituting the network structure may be constituted only of substantially one kind, or may be constituted of two or more kinds.

[Chem. 9]

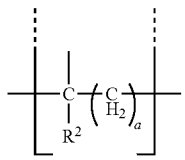

General formula (iia)

[Chem. 10]

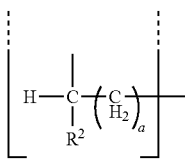

General formula (iib)

It should be noted that a in each of a group represented by the above-mentioned general formula (iia) and a group represented by the above-mentioned general formula (iib) represents 0 or 1. Here, when Y represents a group represented by the general formula (iia), the unit structure represented by the general formula (i) is a unit structure having four bonding sites, and when Y represents a group represented by the general formula (iib), the unit structure is a unit structure having three bonding sites. Y preferably represents a group represented by the general formula (iia) from the following viewpoint: when the ratio at which the hyperbranched polymer is blended into the dental adhesive composition is increased, an increase in its viscosity can be easily suppressed.

In addition, examples of the terminal portion of the network structure formed by the unit structure represented by the general formula (i) include the various atoms and various groups given as the general examples of the terminal portion described in the foregoing.

R¹ constituting the unit structure represented by the general formula (i) represents a divalent saturated aliphatic hydrocarbon group or a divalent aromatic hydrocarbon group. Here, the divalent saturated aliphatic hydrocarbon group may be linear or cyclic. In addition, the number of its carbon atoms, which is not particularly limited, falls within preferably the range of from 1 to 5, more preferably the range of from 1 to 2. Setting the number of carbon atoms to 5 or less shortens a molecular chain portion represented as R¹, and hence can additionally suppress entanglement between the polymerizable monomer containing the acidic group-containing polymerizable monomer constituting the dental adhesive composition and the hyperbranched polymer, and can additionally suppress an increase in viscosity of a liquid or paste-like dental adhesive composition. Examples of the divalent linear saturated aliphatic hydrocarbon group include a methylene group, an ethylene group, a propylene group, and a butylene group. In addition, examples of the divalent cyclic saturated aliphatic hydrocarbon group include a cyclopropylene group and a cyclobutylene group.

In addition, the divalent aromatic hydrocarbon group may be any one of: a monocyclic group containing one benzene ring; a group containing two or more benzene rings and having a condensed ring structure; and a group containing two or more benzene rings and free of any condensed ring structure. The number of benzene rings in the divalent aromatic hydrocarbon group, which is not particularly limited, preferably falls within the range of from 1 to 2, and the number of the benzene rings is particularly preferably 1 (in other words, the divalent aromatic hydrocarbon group is particularly preferably a phenylene group). Setting the number of the benzene rings to 2 or less can additionally suppress the entanglement between the polymerizable monomer containing the acidic group-containing polymerizable monomer constituting the dental adhesive composition and the hyperbranched polymer, and can additionally suppress an increase in viscosity of the dental adhesive composition. Examples of the divalent aromatic hydrocarbon group may include a naphthylene group and a biphenylene group in addition to the phenylene group.

It should be noted that out of R¹'s given above, a phenylene group is particularly preferred. A phenylene group exhibits small adverse effects on handleability in dental therapy with the dental adhesive composition and on the mechanical properties of the cured product thereof even when the blending amount of the hyperbranched polymer to be added to the dental adhesive composition is largely changed. Accordingly, the composition design of the dental adhesive composition can be easily performed without being bound by the handleability and the mechanical properties. In addition, when a phenylene group is used as R¹, the mechanical strength of the cured product obtained by curing the dental adhesive composition can be increased.

Of the hyperbranched polymers each having the network structure formed by the unit structure represented by the general formula (i), for example, a hyperbranched polymer containing a unit structure represented by the following general formula (I), and at least one unit structure selected from a unit structure represented by the following general formula (IIA) and a unit structure represented by the following general formula (IIB) is particularly suitable. Here, the unit structure represented by the general formula (I) is a unit structure having four bonding sites, the unit constituting the network structure itself, and the unit structures represented by the general formula (IIA) and the general formula (IIB) are each a unit structure constituting the terminal portion (terminal group) of the network structure. In the following description, the term "hyperbranched polymer A" refers only to a hyperbranched polymer having a network structure constituted of those unit structures.

[Chem. 11]

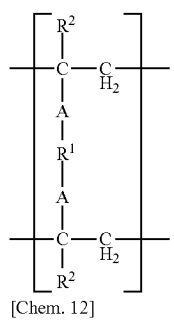

General formula (I)

[Chem. 12]

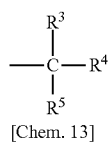

General formula (IIA)

[Chem. 13]

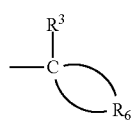

General formula (IIB)

Here, in the general formula (I), A, $R^1$, and $R^2$ are the same as A, $R^1$, and $R^2$ shown in the general formula (i), respectively.

In addition, in the general formula (IIA) and the general formula (IIB), $R^3$, $R^4$, and $R^5$ each represent a hydrogen atom, an alkyl group having a main chain containing 1 to 5 carbon atoms, an alkoxycarbonyl group having a main chain containing 1 to 5 carbon atoms, an aryl group, or a cyano group. In addition, in the general formula (IIB), $R^6$ represents an alkylene group having a main chain containing 4 to 10 carbon atoms.

In particular, $R^3$, $R^4$, and $R^5$, which form the general formula (IIA) and the general formula (IIB), each more preferably represent an alkyl group having a main chain containing 1 to 5 carbon atoms, an alkoxycarbonyl group having a main chain containing 1 to 5 carbon atoms, or a cyano group. Examples of the alkyl group include a methyl group, an ethyl group, and a propyl group, examples of the alkoxycarbonyl group include a methoxycarbonyl group, an ethoxycarbonyl group, and a propoxycarbonyl group, and an example of the aryl group is a phenyl group. It should be noted that when the number of carbon atoms contained in the main chain of each of the alkyl group and the alkoxycarbonyl group is set to 5 or less, especially a methyl group or a methoxycarbonyl group is used, the main chain shortens, and hence entanglement between the polymerizable monomer containing the acidic group-containing polymerizable monomer constituting the dental adhesive composition and the hyperbranched polymer A can be additionally suppressed, and an increase in viscosity of the dental adhesive composition can be additionally suppressed.

In addition, part of the hydrogen atoms of the alkyl group, the alkoxycarbonyl group, and the aryl group may each be substituted with a substituent. Examples thereof may include an alkyl group having 1 to 3 carbon atoms such as a methyl group and an alkoxyl group having 1 to 3 carbon atoms such as a methoxy group. It should be noted that when the number of carbon atoms of each of the alkyl group and the alkoxyl group is set to 3 or less, especially a methyl group or a methoxy group is used, a side chain constituted of the substituent shortens, and hence the entanglement between the polymerizable monomer containing the acidic group-containing polymerizable monomer constituting the dental adhesive composition and the hyperbranched polymer A can be additionally suppressed, and an increase in viscosity of the dental adhesive composition can be additionally suppressed.

$R^6$ constituting the general formula (IIB) represents an alkylene group having a main chain containing 4 to 10 carbon atoms. Examples of the alkylene group include a butylene group, a pentylene group, and a nonylene group. In addition, part of the hydrogen atoms of the alkylene group may each be substituted with a substituent. Examples thereof may include an alkyl group having 1 to 3 carbon atoms such as a methyl group and an alkoxyl group having 1 to 3 carbon atoms such as a methoxy group. It should be noted that setting the number of carbon atoms contained in the main chain of the alkylene group to 4 or more can suppress the strain of a ring constituted of $R^6$ and carbon atoms bonded to both ends of $R^6$. Accordingly, the adhesive force and adhesion durability of the dental adhesive composition are improved, and the coloring or discoloring of a cured product thereof hardly occurs. In addition, setting the number of carbon atoms contained in the main chain of the alkylene group to 10 or less shortens the main chain, or when the number of carbon atoms of the alkyl group or alkoxyl group to be selected as the substituent is set to 3 or less, especially a methyl group or a methoxy group is used, a side chain constituted of the substituent shortens. Accordingly, the entanglement between the polymerizable monomer containing the acidic group-containing polymerizable monomer constituting the dental adhesive composition and the hyperbranched polymer A can be additionally suppressed, and an increase in viscosity of the dental adhesive composition can be additionally suppressed. It should be noted that the alkylene group is particularly preferably a pentylene group from the viewpoint of compatibility between the suppression of the strain of the ring and the suppression of the increase in viscosity.

It should be noted that the first unit structure represented by the general formula (I) or the second unit structure selected from the two kinds of unit structures represented by the general formula (IIA) and the general formula (IIB) can be bonded to each of the four bonding sites of the first unit structure represented by the general formula (I). Further, when the hyperbranched polymer A contains another unit structure (third unit structure) except the general formula (I), the general formula (IIA), and the general formula (IIB), the third unit structure can also be bonded to the four bonding sites. In this case, the network structure is formed by bonding the first unit structures together via at least any one of the four bonding sites. Further, the second unit structure as a terminal group that divides the network structure can be bonded to up to three bonding sites out of the four bonding sites of the first unit structure. In this case, a content ratio (molar ratio) between the first unit structure and the second unit structure contained in the hyperbranched polymer A is not particularly limited, but is controlled within preferably the range of from 3:7 to 7:3, more preferably the range of from 4:6 to 6:4. When the molar ratio is controlled within the range, a network structure having appropriate branches can be formed and a remarkable increase in viscosity of a solution obtained by dispersing the hyperbranched polymer A in a solvent can be suppressed. It should be noted that, when the hyperbranched polymer A also contains the third unit structure having two or more bonding sites, the content ratio (molar ratio) between the first unit structure and the second unit structure, which also depends on the content ratio of the third unit structure with respect to the first unit structure and the second unit structure, is, for example, selected from preferably the range of from 1:9 to 7:3, more preferably the range of from 2:8 to 7:3 in such a range that a network structure can be formed. It should be noted that, also in this case, the content ratio (molar ratio) between the first unit structure and the second unit structure is controlled within still more preferably the range of from 3:7 to 7:3, particularly preferably the range of from 4:6 to 6:4.

Such hyperbranched polymer A containing the unit structure represented by the general formula (I), and at least one unit structure selected from the unit structure represented by the general formula (IIA) and the unit structure represented by the general formula (IIB) as described above is free of a group having a reactive unsaturated bond (such as an acrylate group, an acrylic group, or a styryl group) or a reactive functional group such as an amino group in the molecule. In addition, the polymerizable monomer containing the acidic group-containing polymerizable monomer causes a reactive functional group to disappear through its polymerization reaction. Accordingly, the dental adhesive composition according to this embodiment using the hyperbranched polymer A has an excellent adhesive force and excellent adhesion durability, and even when the composition is exposed to food and drink in an intraoral environment, or is exposed to natural light or indoor light, after having been cured, the cured product hardly colors or discolors.

Moreover, the hyperbranched polymer A containing the unit structure represented by the general formula (I) and at least one unit structure selected from the unit structure represented by the general formula (IIA) and the unit structure represented by the general formula (IIB) has a network structure based on the unit structures represented by the general formulae (IIA) and (IIB). That is, the movement of the branched molecular chain at both terminals is very limited. Therefore, it is very difficult to entangle adjacent branch moieties, and thus an increase in viscosity of the dental adhesive composition hardly occurs. Therefore, large polymerization shrinkage involved in the polymerization does not occur. As a result, a dental adhesive composition having an excellent adhesive force and excellent adhesion durability is obtained.

It should be noted that the hyperbranched polymer A to be suitably used in the dental adhesive composition according to this embodiment may contain, as the third unit structure, at least any one kind of unit structure selected from a unit structure represented by the following general formula (IIIA), a unit structure represented by the following general formula (IIIB), a unit structure represented by the following general formula (IIIC), and a unit structure represented by the following general formula (IIID). It should be noted that the third unit structures represented by the following general formula (IIIA) and the following general formula (IIID) are each contained as an impurity component in the hyperbranched polymer A in synthesizing the hyperbranched polymer A in some cases.

[Chem. 14]

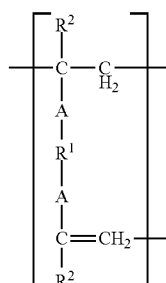

General formula (IIIA)

[Chem. 15]

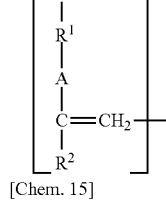

General formula (IIIB)

[Chem. 16]

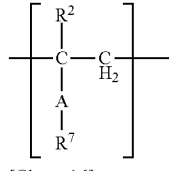

General formula (IIIC)

[Chem. 17]

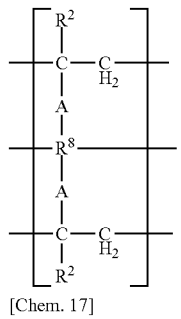

General formula (IIID)

Here, in the general formula (IIIA), the general formula (IIIB), the general formula (IIIC), and the general formula (IIID), A, $R^1$, and $R^2$ are the same as A, $R^1$, and $R^2$ shown in the general formula (i), respectively. In addition, in the general formula (IIIB), $R^7$ represents a monovalent saturated aliphatic hydrocarbon group or a monovalent aromatic hydrocarbon group, in the general formula (IIIC), $R^8$ represents a tetravalent saturated aliphatic hydrocarbon group or a tetravalent aromatic hydrocarbon group, and in the general formula (IIID), B represents —COO—CH=.

In addition, a ratio between such a third unit structure having two bonding sites as given in each of the general formula (IIIA) and the general formula (IIIB), and the first unit structure represented by the general formula (I) falls within preferably the range of from 6:4 to 0:10, more preferably the range of from 4:6 to 0:10, and is most preferably 0:10. Setting the ratio between the third unit structure having two bonding sites and the first unit structure represented by the general formula (I) within the range can result in the formation of a network structure having appropriate branches and can suppress a remarkable increase in viscosity of the adhesive composition blended with the hyperbranched polymer A.

As each of $R^7$ constituting the third unit structure represented by the general formula (IIIB) and $R^8$ constituting the third unit structure represented by the general formula (IIIC), one having the same structure as that of $R^1$ except that there is a difference in valence may be utilized.

It should be noted that the second unit structure represented by each of the general formula (IIA) and the general formula (IIB) is a structure derived from a raw material component (e.g., a monomer, a polymerization initiator, or a terminal group modifier) to be used in a synthesis process for the hyperbranched polymer A to be used in the dental adhesive composition according to this embodiment. The raw material component is not particularly limited, and is exemplified by a known polymerization initiator, preferably an azo-based polymerization initiator disclosed in WO 2010/126140 A1. In this regard, however, in the dental adhesive composition according to this embodiment, out of the raw material component, polymerization initiator, or azo-based polymerization initiator listed above, there is preferably adopted one that can have a structure represented by the general formula (IIA) and/or the general formula (IIB) after the completion of the synthesis of the hyperbranched polymer A. Accordingly, the adhesive force and adhesion durability of the dental adhesive composition according to this embodiment are improved, and the coloring or discoloring of a cured product thereof hardly occurs.

Specific examples of the second unit structure represented by the general formula (IIA) include the following structural formula A to structural formula K, and specific examples of the second unit structure represented by the general formula (IIB) include the following structural formula L and structural formula M. Such second unit structure represented by each of the structural formula A to the structural formula M is particularly suitable in terms of easy availability of the hyperbranched polymer A.

[Chem. 18]

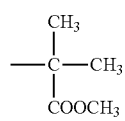
Structural formula A

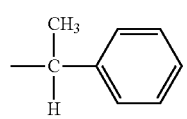
Structural formula B

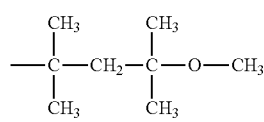
Structural formula C

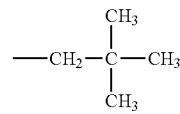
Structural formula D

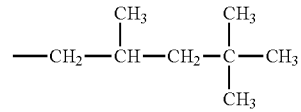
Structural formula E

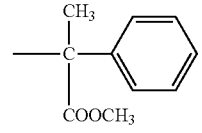
Structural formula F

[Chem. 19]

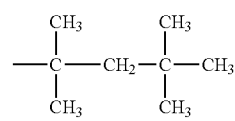
Structural formula G

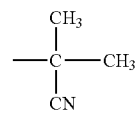
Structural formula H

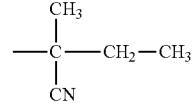
Structural formula I

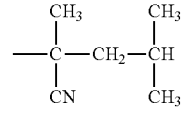
Structural formula J

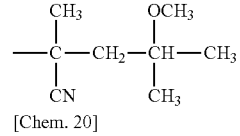
Structural formula K

[Chem. 20]

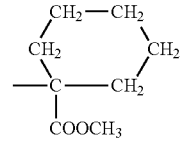
Structural formula L

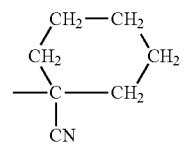
Structural formula M

Examples of the hyperbranched polymer A having the molecular structure as described above include ones shown in the following items (1) to (6).

(1) Hyperbranched polymer disclosed in T. Hirano et al., J. Appl. Polym. Sci., 2006, 100, 664-670 (A: single bond for bonding C and R', $R^4$: phenylene group, $R^2$: hydrogen atom, $R^3$: —$CH_3$, $R^4$: —$CH_3$, $R^5$: —$COOCH_3$). It should be noted that HYPERTECH™/HA-DVB-500 (manufactured by NISSAN CHEMICAL INDUSTRIES, LTD., molecular weight determined by GPC method: 48,000, hydrodynamic mean diameter: 11.7 nm (in THF)) is given as a commercially available hyperbranched polymer having substantially the same molecular structure.

(2) Hyperbranched polymer disclosed in T. Hirano et al., Macromol. Chem. Phys., 205, 206, 860-868 (A: —COO—, $R^1$: —$(CH_2)_2$—, $R^2$: —$CH_3$, $R^3$: —$CH_3$, $R^4$: —$CH_3$, $R^5$: —$COOCH_3$). It should be noted that, as a commercially available hyperbranched polymer having substantially the same molecular structure, there are given HYPERTECH™; HA-DMA-200 (molecular weight determined by GPC method: 22,000, hydrodynamic mean diameter: 5.2 nm (in THF)), HA-DMA-50 (trial sample, molecular weight determined by GPC method: 4,000), and HA-DMA-700 (trial sample, molecular weight determined by GPC method: 67,000), all of which are manufactured by NISSAN CHEMICAL INDUSTRIES, LTD.

(3) Hyperbranched polymer disclosed in T. Sato et al., Macromolecules, 2005, 38, 1627-1632 (A: —COO—, $R^4$: —$(CH_2)_4$—, $R^2$: —H, $R^3$: —$CH_3$, $R^4$: —$CH_3$, $R^5$: —$COOCH_3$).

(4) Hyperbranched polymer disclosed in T. Sato et al., Macromole. Mater. Eng., 2006, 291, 162-172. It should be noted that this hyperbranched polymer contains the third unit structure represented by the general formula (IIIB). In this case, in the first unit structure represented by the general formula (I), A, $R^1$, and $R^2$ represent a single bond for bonding C and $R^1$, a phenylene group, and —H, respectively, and in the third unit structure represented by the general formula (IIIB), A, $R^7$, and $R^2$ represent —COO—, an ethyl group, and —H, respectively. In addition, in the second unit structure represented by the general formula (IIA), $R^3$, $R^4$, and $R^5$ represent —$CH_3$, —$CH_3$, and —$COOCH_3$, respectively.

(5) Hyperbranched polymer disclosed in T. Sato et al., Polym. Int. 2004, 53, 1138-1144. It should be noted that this hyperbranched polymer contains the third unit structure represented by the general formula (IIIB). In this case, in the first unit structure represented by the general formula (I), A, $R^1$, and $R^2$ represent —COO—, —$(CH_2)_4$—, and —H, respectively and in the third unit structure represented by the general formula (IIIB), A, $R^7$, and $R^2$ represent —O—, a 2-methylpropyl group, and —H, respectively. In addition, in the second unit structure represented by the general formula (IIA), $R^3$, $R^4$, and $R^5$ represent —$CH_3$, —$CH_3$, and —CN, respectively.

(6) Hyperbranched polymer disclosed in T. Sato et al., J. Appl. Polym. Sci. 2006, 102, 408. It should be noted that this hyperbranched polymer contains the third unit structure represented by the general formula (IIID). In this case, in the first unit structure represented by the general formula (I), A, $R^1$, and $R^2$ represent —COO—$CH_2$—, a phenylene group (the two bonding sites are at ortho positions), and —H, respectively and in the third unit structure represented by the general formula (IIID), A, B, $R^1$, and $R^2$ represent —COO—$CH_2$—, —COO—CH=, a phenylene group (the two bonding sites are at ortho positions), and —H, respectively. In addition, in the second unit structure represented by the general formula (IIA), $R^3$, $R^4$, and $R^5$ represent —$CH_3$, —$CH_3$, and —$COOCH_3$, respectively.

In addition, various hyperbranched polymers commercially available at present including the hyperbranched polymer A include "Hybrane™" manufactured by DSM and "Boltorn™" manufactured by Perstorp in addition to the "HYPERTECH™" series manufactured by Nissan Chemical Industries, Ltd. It should be noted that with regard to each of the "HYPERTECH", the "Hybrane", and the "Boltorn", grades having different molecular weights, viscosities, and terminal groups have been sold. Here, with regard to the HYPERTECH series, as a hyperbranched polymer having a network structure formed of the unit structure represented by the general formula (i) except the hyperbranched polymer A, there exists, for example, HPS-200 (Y represents a group represented by the general formula (iib) and the network structure is formed of a unit structure having three bonding sites).

Next, constituent materials for the dental adhesive composition except (A) the polymerizable monomer containing the acidic group-containing polymerizable monomer and (B) the dendritic polymer are described.

—(C) Water—

The dental adhesive composition according to this embodiment is preferably blended with water. Blending the dental adhesive composition according to this embodiment with the water exhibits the following effects: an affinity for the tooth is improved by a combination with the acidic group-containing polymerizable monomer; and a decalcifying (etching) action on the tooth improves to increase an adhesive strength to the tooth. It is particularly effective to incorporate the water into a dental adhesive primer or a dental adhesive bonding material. It is preferred that the water be substantially free of impurities harmful to storage stability, biocompatibility, and adhesive property, and examples thereof include purified water, deionized water, and distilled water.

The blending amount of (C) the water in the dental adhesive composition according to this embodiment is not particularly limited and may be appropriately set. However, when the amount of (C) the water is excessively large, the mechanical strength of the cured body tends to reduce or the storage stability of the composition tends to reduce. Accordingly, in consideration of a balance with an effect of blending the water, the blending amount falls within preferably the range of from 0.2 part by mass to 150 parts by mass, more preferably the range of from 0.5 part by mass to 130 parts by mass with respect to 100 parts by mass of the total of (A) the polymerizable monomer containing the acidic group-containing polymerizable monomer and (B) the dendritic polymer. In addition, when the dental adhesive composition contains the water, the ratios at which the remaining components except a component insoluble in the water and an oily component like a filler out of the various components in the dental adhesive composition, i.e., the oily component and the water are blended are not particularly limited and may be appropriately selected depending on the applications of the dental adhesive composition. However, for example, the amount of the water is preferably set to fall within the range of from 3 parts by mass to 30 parts by mass with respect to 100 parts by mass of the oily component, and the amount of the water is more preferably set to fall within the range of from 5 parts by mass to 20 parts by mass with respect to 100 parts by mass of the oily component. It should be noted that when the dental adhesive composition according to this embodiment contains the water, for example, the dental adhesive composition may be a water-in-oil emulsion in which the oily component forms a continuous phase and an aqueous component forms a discontinuous droplet, may be an oil-in-water emulsion in which the oily component forms a discontinuous droplet and the aqueous component forms a continuous phase, or may be a composition in which the oily component and the water uniformly mix with each other. It should be noted that main components constituting the oily component include the polymerizable monomer and the dendritic polymer.

—(D) Polymerization Initiator—

The dental adhesive composition according to this embodiment is preferably blended with a polymerization initiator. When the dental adhesive composition is blended with the polymerization initiator, the dental adhesive composition can be polymerized and cured alone. As the polymerization initiator, (D1) a photopolymerization initiator, (D2) a chemical polymerization initiator, or (D3) a thermal polymerization initiator may be used, and two or more kinds of polymerization initiators may also be utilized in combination. It should be noted that, when the fact that the dental adhesive composition is generally used in the oral cavity is taken into consideration, it is preferred to use at least one kind selected from a photopolymerization initiator and a chemical polymerization initiator out of the three kinds of polymerization initiators. In ordinary cases, the chemical polymerization-type polymerization initiator is used in a dental adhesive resin cement, and the photopolymerization-type polymerization initiator is used in each of the dental adhesive bonding material, a dental adhesive composite resin, and the dental adhesive resin cement.

The blending amount of (D) the polymerization initiator in the dental adhesive composition according to this embodiment is not particularly limited and may be appropriately set. However, the blending amount falls within preferably the range of from 0.001 part by mass to 10 parts by mass, more preferably the range of from 0.005 part by mass to 7.5 parts by mass, most preferably the range of from 0.01 part by mass to 5 parts by mass with respect to 100 parts by mass of the total of (A) the polymerizable monomer containing the acidic group-containing polymerizable monomer and (B) the dendritic polymer. When (D) the polymerization initiator is (D1) the photopolymerization initiator out of the polymerization initiators, its blending amount falls within preferably the range of from 0.001 part by mass to 2.5 parts by mass, more preferably the range of from 0.005 part by mass to 2 parts by mass, most preferably the range of from 0.01 part by mass to 1.75 parts by mass.

The three kinds of polymerization initiators are described in more detail below.

As (D1) the photopolymerization initiator, a known one to be used as a dental material may be used without any limitation. Typical examples of the photopolymerization initiator include photopolymerization initiators such as: combinations of α-diketones and tertiary amines; acylphosphine oxides; combinations of acylphosphine oxides and tertiary amines; combinations of thioxanthones and tertiary amines; combinations of α-aminoacetophenones and tertiary amines: and combinations of aryl borates and photo acid generators.

The various compounds to be suitably used in the various photopolymerization initiators are exemplified below. Examples of the α-diketones include camphorquinone, benzil, α-naphthyl, acetonaphthone, naphthoquinone, p,p'-dimethoxybenzil, p,p'-dichlorobenzyl acetyl, 1,2-phenanthrenequinone, 1,4-phenanthrenequinone, 3,4-phenanthrenequinone, and 9,10-phenanthrenequinone.

Examples of the tertiary amines include N,N-dimethylaniline, N,N-diethylaniline, N,N-di-n-butylaniline, N,N-dibenzylaniline, N,N-dimethyl-p-toluidine, N,N-diethyl-p-toluidine, N,N-dimethyl-m-toluidine, p-bromo-N,N-dimethylaniline, m-chloro-N,N-dimethylaniline, p-dimethylaminobenzaldehyde, p-dimethylaminoacetophenone, p-dimethylaminobenzoic acid, p-dimethylaminobenzoic acid ethyl ester, p-dimethylaminobenzoic acid amyl ester, N,N-dimethylanthranilic acid methyl ester, N,N-dihydroxyethylaniline, N,N-dihydroxyethyl-p-toluidine, p-dimethylaminophenethyl alcohol, p-dimethylaminostilbene, N,N-dimethyl-3,5-xylidine, 4-dimethylaminopyridine, N,N-dimethyl-α-naphthylamine, N,N-dimethyl-β-naphthylamine, tributylamine, tripropylamine, triethylamine, N-methyldiethanolamine, N-ethyldiethanolamine, N,N-dimethylhexylamine, N,N-dimethyldodecylamine, N,N-dimethylstearylamine, N,N-dimethylaminoethyl methacrylate, N,N-diethylaminoethyl methacrylate, and 2,2'-(n-butylimino) diethanol. One kind of those amines may be used alone, or two or more kinds thereof may be used as a blend.

Examples of the acylphosphine oxides include benzoyldiphenylphosphine oxide, 2,4,6-trimethylbenzoyldiphenylphosphine oxide, 2,6-dimethoxybenzoyldiphenylphosphine oxide, 2,6-dichlorobenzoyldiphenylphosphine oxide, and 2,3,5,6-tetramethylbenzoyldiphenylphosphine oxide.

Examples of the thioxanthones include 2-chlorothioxanthone and 2,4-diethylthioxanthone.

Examples of the α-aminoacetophenones include 2-benzyl-dimethylamino-1-(4-morpholinophenyl)-butanone-1,2-benzyl-diethylamino-1-(4-morpholinophenyl)-butanone-1, 2-benzyl-dimethylamino-1-(4-morpholinophenyl)-propanone-1,2-benzyl-diethylamino-1-(4-morpholinophenyl)-propanone-1,2-benzyl-dimethylamino-1-(4-morpholinophenyl)-pentanone-1, and 2-benzyl-diethylamino-1-(4-morpholinophenyl)-pentanone-1.

One kind of the photopolymerization initiators may be used alone, or two or more kinds thereof may be used as a mixture.

(D2) The chemical polymerization initiator is a polymerization initiator that is formed of two or more components and generates a polymerization active species at around room temperature when all the components are mixed immediately before use. Examples thereof include polymerization initiators formed of any of various combinations such as an organic peroxide/an amine, an organic peroxide/an amine/an organic sulfinic acid, an organic peroxide/an amine/an aryl borate, an aryl borate/an acidic compound, and a barbituric acid derivative/a copper compound/a halide.

In the dental adhesive composition according to this embodiment, a chemical polymerization initiator formed of an organic peroxide and an amine is suitable because a high adhesive strength to the tooth is obtained and its handling is easy. In particular, the chemical polymerization initiator formed of the organic peroxide and the amine has the following advantage: part of the amine is neutralized by the acidic group-containing polymerizable monomer (a1), and as a result, the curing rate is moderately slowed and an operation of removing excess cement becomes easy.

Typical examples of the organic peroxide include ketone peroxides, peroxyketals, hydroperoxides, dialkylperoxides, diacyl peroxides, peroxydicarbonates, peroxyesters, and diarylperoxides.

The organic peroxide is specifically exemplified below. Examples of the ketone peroxides include methyl ethyl ketone peroxide, cyclohexanone peroxide, methylcyclohexanone peroxide, methyl acetoacetate peroxide, and acetylacetone peroxide.

Examples of the peroxyketals include 1,1-bis(t-hexylperoxy)3,3,5-trimethylcyclohexane, 1,1-bis(t-hexylperoxy)cyclohexane, 1,1-bis(t-butylperoxy)3,3,5-trimethylcyclohexanone, 1,1-bis(t-butylperoxy)cyclohexane, 1,1-bis(t-butylperoxy)cyclodecane, 2,2-bis(t-butylperoxy)butane, n-butyl 4,4-bis(t-butyl peroxy)valerate, and 2,2-bis(4,4-di-t-butylperoxycyclohexyl)propane.

Examples of the hydroperoxides include P-methane hydroperoxide, diisopropylbenzene peroxide, 1,1,3,3-tetramethylbutyl hydroperoxide, cumene hydroperoxide, t-hexyl hydroperoxide, and t-butyl hydroperoxide.

Examples of the dialkyl peroxides include α,α-bis(t-butylperoxy)diisopropylbenzene, dicumyl peroxide, 2,5-dimethyl-2,5-bis(t-butylperoxy)hexane, t-butylcumylperoxide, di-t-butyl peroxide, and 2,5-dimethyl-2,5-bis(t-butylperoxy)hexane-3.

Examples of the diacyl peroxides include isobutyryl peroxide, 2,4-dichlorobenzoyl peroxide, 3,5,5-trimethylhexanoyl peroxide, octanoyl peroxide, lauroyl peroxide, stearyl peroxide, succinic acid peroxide, m-toluoyl benzoyl peroxide, and benzoyl peroxides.

Examples of the peroxycarbonates include di-n-propyl peroxydicarbonate, diisopropyl peroxydicarbonate, bis(4-t-butylcyclohexyl) peroxydicarbonate, di-2-ethoxyethyl peroxydicarbonate, di-2-ethylhexyl peroxydicarbonate, di-2-methoxybutyl peroxydicarbonate, and di(3-methyl-3-methoxybutyl) peroxydicarbonate.

Examples of the peroxyesters include α,α-bis(neodecanoylperoxy)diisopropylbenzene, cumyl peroxyneodecanoate, 1,1,3,3-tetramethylbutyl peroxyneodecanoate, 1-cyclohexyl-1-methylethyl peroxyneodecanoate, t-hexyl peroxyneodecanoate, t-butyl peroxyneodecanoate, t-hexyl peroxypivalate, t-butyl peroxypivalate, 1,1,3,3-tetramethylbutyl peroxy-2-ethylhexanonate, 2,5-dimethyl-2,5-bis(2-ethylhexanoylperoxy)hexane, 1-cyclohexyl-1-methylethyl peroxy-2-ethylhexanonate, t-hexyl peroxy-2-ethylhexanonate, t-butyl peroxy-2-ethylhexanonate, t-butyl peroxyisobutyrate, t-hexyl peroxyisopropylmonocarbonate, t-butyl peroxymaleic acid, t-butyl peroxy-3,5,5-trimethylhexanonate, t-butyl peroxylaurate, 2,5-dimethyl-2,5-bis(m-toluoylperoxy)hexane, t-butyl peroxyisopropylmonocarbonate, t-butyl peroxy-2-ethylhexylmonocarbonate, t-hexyl peroxybenzoate, 2,5-dimethyl-2,5bis(benzoylperoxy)hexane, t-butylperoxyacetate, t-butyl peroxy-m-toluoylbenzoate, t-butyl peroxybenzoate, and bis(t-butyl peroxy)isophthalate.

In addition, for example, t-butyltrimethylsilyl peroxide or 3,3',4,4'-tetra(t-butylperoxycarbonyl)benzophenone may be used as the suitable organic peroxide.

The organic peroxide to be used only needs to be appropriately selected and used. One kind of the organic peroxides may be used alone, or two or more kinds thereof may be used in combination. Of those, hydroperoxides, ketone peroxides, peroxyesters, and diacyl peroxides are particularly preferred from the viewpoint of a polymerization activity. In addition, of those, it is preferred to use an organic peroxide having a 10-hour half-life temperature of 60° C. or more from the viewpoint of storage stability of the dental adhesive composition.

On the other hand, the amine to be combined with the organic peroxide is not particularly limited, but examples thereof include secondary and tertiary aromatic amines in each of which an amino group is bonded to an aromatic group such as an aryl group or a pyridyl group. Examples of the secondary aromatic amine that may be suitably used include N-methylaniline, N-(2-hydroxyethyl) aniline, and N-methyl-p-toluidine. In addition, examples of the tertiary aromatic amine that may be suitably used include N,N-dimethylaniline, N,N-diethylaniline, N,N-di-n-butylaniline, N,N-dibenzylaniline, N-methyl-N-(2-hydroxyethyl)aniline, N,N-di(2-hydroxyethyl)aniline, p-bromo-N,N-dimethylaniline, p-chloro-N,N-dimethylaniline, N,N-dimethyl-p-toluidine, N,N-diethyl-p-toluidine, p-tolyldiethanolamine, N-methyl-N-(2-hydroxyethyl)-p-toluidine, p-dimethylaminobenzaldehyde, p-dimethylaminoacetophenone, p-dimethylaminobenzoic acid, p-dimethylaminobenzoic acid ethyl ester, p-dimethylaminobenzoic acid amyl ester, N,N-dimethylanthranilic acid methyl ester, p-dimethylaminophenethyl alcohol, N,N-dimethyl-3,5-xylidine, 4-dimethylaminopyridine, N,N-dimethyl-α-naphthylamine, and N,N-dimethyl-β-naphthylamine. Of those amine compounds, p-tolyldiethanolamine and N,N-dimethyl-p-toluidine are particularly suitably used from the viewpoint of curability. In the chemical polymerization initiator formed of the organic peroxide and the amine using the various compounds in combination, the amine is used in an amount within the range of desirably from 0.01 mol to 4 mol, particularly desirably from 0.05 mol to 3 mol per 1 mol of the organic peroxide.

A system in which a sulfinic acid such as benzenesulfinic acid or p-toluenesulfinic acid and a salt thereof is added to the initiator system formed of the organic peroxide and the amine compound, or a system in which a barbituric acid-based initiator such as 5-butylbarbituric acid is blended in the initiator system may also be used without any problem.

Further, an aryl borate compound/acidic compound-based polymerization initiator utilizing such a phenomenon that an aryl borate compound is decomposed by an acid to generate a radical may also be used.

The aryl borate compound is not particularly limited, and a known compound may be used as long as the compound has at least one boron-aryl bond in the molecule. Of those, it is preferred to use an aryl borate compound having 3 or 4 boron-aryl bonds in one molecule in consideration of storage stability, and it is more preferred to use an aryl borate compound having 4 boron-aryl bonds from the viewpoints of handling and easy synthesis and availability.

Examples of the borate compound having 3 boron-aryl bonds in one molecule may include sodium salts, lithium salts, potassium salts, magnesium salts, tetrabutylammonium salts, tetramethylammonium salts, tetraethylammonium salts, tributylamine salts, triethanolamine salts, methylpyridinium salts, ethylpyridinium salts, butylpyridinium salts, methylquinolinium salts, ethylquinolinium salts, or butylquinolinium salts of a monoalkyltriphenylboron, a monoalkyltris(p-chlorophenyl) boron, a monoalkyltris(p-fluorophenyl)boron, a monoalkyltris(3,5-bistrifluoromethyl) phenylboron, a monoalkyltris[3,5-bis(1,1,1,3,3,3-hexafluoro-2-methoxy-2-propyl)phenyl]boron, a monoalkyltris(p-nitrophenyl)boron, a monoalkyltris(m-nitrophenyl)boron, a monoalkyltris(p-butylphenyl)boron, a monoalkyltris(m-butylphenyl)boron, a monoalkyltris(p-butyloxyphenyl)boron, a monoalkyltris(m-butyloxyphenyl)boron, a monoalkyltris(p-octyloxyphenyl)boron, and a monoalkyltris(m-octyloxyphenyl)boron (provided that the alkyl is any one of n-butyl, n-octyl, and n-dodecyl in each of the compounds).

Examples of the borate compound having 4 boron-aryl bonds in one molecule may include sodium salts, lithium salts, potassium salts, magnesium salts, tetrabutylammonium salts, tetramethylammonium salts, tetraethylammonium salts, tributylamine salts, triethanolamine salts, methylpyridinium salts, ethylpyridinium salts, butylpyridinium salts, methylquinolinium salts, ethylquinolinium salts, or butylquinolinium salts of tetraphenylboron, tetrakis(p-chlorophenyl)boron, tetrakis(p-fluorophenyl)boron, tetrakis(3,5-bistrifluoromethyl)phenylboron, tetrakis[3,5-bis(1,1,1,3,3,3-hexafluoro-2-methoxy-2-propyl)phenyl]boron, tetrakis(p-nitrophenyl)boron, tetrakis(m-nitrophenyl)boron, tetrakis(p-butylphenyl)boron, tetrakis(m-butylphenyl)boron, tetrakis (p-butyloxyphenyl)boron, tetrakis(m-butyloxyphenyl) boron, tetrakis(p-octyloxyphenyl)boron, and tetrakis(m-octyloxyphenyl)boron (provided that the alkyl is any one of n-butyl, n-octyl, or n-dodecyl in each of the compounds).

The various aryl borate compounds exemplified above may be used in combination of two or more kinds thereof.

The aryl borate compound/acidic compound-based polymerization initiator is also suitably used in combination with an organic peroxide and/or a transition metal compound. The organic peroxide is as described above. The transition metal compound is suitably a +IV-valent and/or +V-valent vanadium compound. Specific examples of the +IV-valent and/or +V-valent vanadium compound include vanadium compounds such as divanadium(IV) tetroxide, vanadium(IV) oxide acetylacetonate, vanadyl(IV) oxalate, vanadyl(IV) sulfate, oxobis(1-phenyl-1,3-butanedionato)vanadium(IV), bis(maltolato)oxovanadium(IV), vanadium(V) petoxide, sodium metavanadate(V), and ammonium metavanadate(V).

In addition, examples of (D3) the thermal polymerization initiator include: peroxides such as benzoyl peroxide, p-chlorobenzoyl peroxide, tert-butyl peroxy-2-ethylhexanoate, tert-butyl peroxydicarbonate, and diisopropyl peroxydicarbonate; azo compounds such as azobisisobutyronitrile; boron compounds such as tributylborane, tributylborane partial oxide, sodium tetraphenylborate, sodium tetrakis(p-fluorophenyl)borate, and triethanolamine tetraphenylborate; barbituric acids such as 5-butylbarbituric acid and 1-benzyl-5-phenylbarbituric acid; and sulfinates such as sodium benzenesulfinate and sodium p-toluenesulfinate.

(E) —Filler—

It is preferred to blend a filler in the dental adhesive composition according to this embodiment. An effect of suppressing polymerization shrinkage upon polymerization can be increased more by blending a filler in the dental adhesive composition according to this embodiment. Further, through use of the filler, the handleability of the dental adhesive composition can be improved, or the mechanical properties of a cured product thereof can be improved.

As the filler, a known inorganic filler or organic-inorganic composite filler to be used as a filler for a dental material is used without any limitation. Examples of the inorganic filler include metal oxides such as quartz, silica, alumina, silica-titania, silica-zirconia, lanthanum glass, barium glass, and strontium glass. Further, as a cation releasing inorganic filler, silicate glass, fluoroaluminosilicate glass, or the like may be used as necessary. One kind of those inorganic fillers may be used alone, or two or more kinds thereof may be used as a mixture.

Further, as the organic-inorganic composite filler, there may be utilized a particulate product obtained by adding a polymerizable monomer to the inorganic filler exemplified above to prepare a paste, followed by polymerization, and pulverizing the resultant polymerization product.

The particle diameter of such filler is not particularly limited, and a filler having an average particle diameter of from 0.01 μm to 100 μm (particularly preferably from 0.01 μm to 5 μm) to be generally used as a dental material may be appropriately used depending on purposes. Further, the refractive index of the filler is also not particularly limited, a refractive index of a general dental inorganic filler, i.e., a refractive index of from 1.4 to 1.7 may be used without any limitation, and the refractive index only needs to be appropriately set depending on purposes. A plurality of inorganic fillers having different particle diameter ranges and refractive indices may be used in combination.

Further, from the viewpoint of improving the surface glossing property of a cured product obtained by curing the dental adhesive composition, it is preferred to use a spherical inorganic filler.

The inorganic filler is preferably treated with a surface treatment agent typified by a silane coupling agent. In this case, the affinity between the inorganic filler and the radically polymerizable monomer increases, and the mechanical strength and water resistance of the cured product can be improved. The surface treatment may be carried by a known method. In addition, as the silane coupling agent, there is suitably used methyltrimethoxysilane, methyltriethoxysilane, methyltrichlorosilane, dimethyldichlorosilane, trimethylchlorosilane, vinyltrichlorosilane, vinyltriethoxysilane, vinyltris(β-methoxyethoxy)silane, γ-methacryloyloxypropyltrimethoxysilane, γ-chloropropyltrimethoxysilane, γ-glycidoxypropyltrimethoxysilane, hexamethyldisilazane, or the like.

Although the blending amount of any such filler only needs to be appropriately determined depending on use purposes in consideration of the viscosity and the mechanical properties of the cured product when the filler is mixed with (A) the polymerizable monomer containing the acidic group-containing polymerizable monomer and (B) the dendritic polymer, the filler is preferably used in an amount of not more than 500 parts by weight with respect to 100 parts by mass of the total of (A) the polymerizable monomer containing the acidic group-containing polymerizable monomer and (B) the dendritic polymer. In addition, the proper amount of the filler varies depending on applications, and in the applications of the dental adhesive primer and the dental adhesive bonding material, the amount falls within preferably the range of from 2 parts by mass to 30 parts by mass, more preferably the range of from 5 parts by mass to 20 parts by mass with respect to 100 parts by mass of the total of (A) the polymerizable monomer containing the acidic group-containing polymerizable monomer and (B) the dendritic polymer. In the applications of the dental adhesive composite resin and the dental adhesive resin cement, the amount falls within preferably the range of from 100 parts by mass to 500 parts by mass, more preferably the range of from 150 parts by mass to 450 parts by mass with respect to 100 parts by mass of the total of (A) the polymerizable monomer containing the acidic group-containing polymerizable monomer and (B) the dendritic polymer.

—Other Addition Component—

In addition to the polymerizable monomer containing the acidic group-containing polymerizable monomer, the dendritic polymer, the water, the polymerization initiator, and the filler, any other component may be further added to the dental adhesive composition according to this embodiment as required.

For example, the composition may be blended with a water-soluble organic solvent. A known organic solvent may be used as the water-soluble organic solvent without any limitation as long as the solvent shows water solubility. The term "water-soluble" as used herein means that the solubility of the solvent in water at 20° C. is 20 g/100 ml or more. Specific examples of such water-soluble organic solvent include methanol, ethanol, propanol, isopropyl alcohol, acetone, and methyl ethyl ketone. A plurality of those organic solvents may be used as a mixture as required. Ethanol, propanol, isopropyl alcohol, or acetone is preferred in consideration of toxicity to a living body.

In addition, a coloring material such as a pigment, a fluorescent pigment, or a dye may be added for matching the color tone of the cured product with the color tone of a tooth. In addition, a UV absorber may be added for preventing the cured body from discoloring owing to UV light. In addition, a known additive such as a polymerization inhibitor, an antioxidant, an organic solvent, a thickener, a sulfur-containing compound for bonding a metal prosthesis, or a chain transfer agent for regulating the curing time of the dental adhesive resin cement may be used as required.

—Method of Producing Dental Adhesive Composition—

A method of producing the dental adhesive composition according to this embodiment is not particularly limited and a known method of producing a polymerization-type composition may be employed. In general, the dental adhesive composition according to this embodiment may be obtained by: weighing predetermined amounts of the respective components to be blended; and mixing or kneading the components until the mixture becomes uniform.

Hereinafter, a dental adhesive primer, dental adhesive bonding material, dental adhesive composite resin, and dental adhesive resin cement as suitable utilization forms of the dental adhesive composition according to this embodiment are described. However, the utilization forms of the dental adhesive composition according to this embodiment are not limited to embodiments to be described below.

—Dental Adhesive Primer—

A dental adhesive primer (self-etching primer) according to one embodiment of the present invention includes (A) a polymerizable monomer containing an acidic group-containing polymerizable monomer, (B) a dendritic polymer, and (C) water. The adhesive strength and adhesion durability of the dental adhesive primer according to this embodiment can be improved by blending (A) the polymerizable monomer containing the acidic group-containing polymerizable monomer, (B) the dendritic polymer, and (C) the water in combination.

The blending amount of the acidic group-containing polymerizable monomer in the dental adhesive primer falls within preferably the range of from 10 parts by mass to 70 parts by mass, more preferably the range of from 20 parts by mass to 65 parts by mass, most preferably the range of from 30 parts by mass to 60 parts by mass with respect to 100 parts by mass of the total of (A) the polymerizable monomer containing the acidic group-containing polymerizable monomer and (B) the dendritic polymer. Setting the blending amount of the acidic group-containing polymerizable monomer to 10 parts by mass or more facilitates the securement of the adhesive force to the enamel. In addition, setting the blending amount of the acidic group-containing polymerizable monomer to 70 parts by mass or less facilitates the suppression of a reduction in its adhesive force to the dentin.

In addition, the blending amount of (B) the dendritic polymer in the dental adhesive primer falls within preferably the range of from 5 parts by mass to 40 parts by mass, more preferably the range of from 7 parts by mass to 35 parts by mass, most preferably the range of from 10 parts by mass to 30 parts by mass with respect to 100 parts by mass of the total of (A) the polymerizable monomer containing the acidic group-containing polymerizable monomer and (B) the dendritic polymer. Setting the blending amount of (B) the dendritic polymer to 5 parts by mass or more facilitates the securement of the adhesive strength and the adhesion durability. In addition, setting the blending amount of (B) the dendritic polymer to 40 parts by mass or less facilitates the maintenance of the dispersion stability of the dendritic polymer during the storage of a dental adhesive primer liquid.

In addition, the blending amount of (C) the water in the dental adhesive primer falls within preferably the range of from 5 parts by mass to 150 parts by mass, more preferably the range of from 10 parts by mass to 130 parts by mass, most preferably the range of from 15 parts by mass to 110 parts by mass with respect to 100 parts by mass of the total of (A) the polymerizable monomer containing the acidic group-containing polymerizable monomer and (B) the dendritic polymer.

Setting the blending amount of the water to 5 parts by mass or more can exhibit a decalcifying force on the bonding object and facilitates an improvement in penetrability into the bonding object. In addition, setting the blending amount of the water to 150 parts by mass or less facilitates the securement of its handleability and the suppression of a reduction in its adhesive force to the bonding object.

It should be noted that the materials described in the foregoing may be suitably used as (A) the polymerizable monomer containing the acidic group-containing polymerizable monomer, (B) dendritic polymer, and (C) water in the dental adhesive primer according to this embodiment, and their description is omitted here. In addition, any other component as well as the polymerizable monomer containing the acidic group-containing polymerizable monomer, the dendritic polymer, and the water may be further added to the dental adhesive primer according to this embodiment as required. The primer may be blended with, for example, the water-soluble organic solvent, the polymerization inhibitor, or the filler as required.

—Dental Adhesive Bonding Material—

A dental adhesive bonding material (self-etching bonding material) according to one embodiment of the present invention includes (A) a polymerizable monomer containing an acidic group-containing polymerizable monomer, (B) a dendritic polymer, (C) water, and (D) a polymerization initiator. The adhesive force and adhesion durability of the dental adhesive bonding material according to this embodiment can be improved by blending the polymerizable monomer containing the acidic group-containing polymerizable monomer, the dendritic polymer, the water, and the polymerization initiator in combination. This is probably because when the dendritic polymer is used, large polymerization shrinkage involved in the polymerization of the polymerizable monomer containing the acidic group-containing polymerizable monomer hardly occurs and hence the shrinkage stress of the polymerizable monomer containing the acidic group-containing polymerizable monomer is suppressed. Accordingly, a reduction in adhesive force of the polymerizable monomer containing the acidic group-containing polymerizable monomer to the bonding object, the adhesive force competing with a polymerization shrinkage stress caused upon curing of the polymerizable monomer containing the acidic group-containing polymerizable monomer at the interface with the bonding object, can be suppressed. As a result, the original adhesive force of the polymerizable monomer containing the acidic group-containing polymerizable monomer to the bonding object can be exhibited.

The blending amount of the acidic group-containing polymerizable monomer in the dental adhesive bonding material falls within preferably the range of from 7 parts by mass to 60 parts by mass, more preferably the range of from 12 parts by mass to 50 parts by mass, most preferably the range of from 15 parts by mass to 35 parts by mass with respect to 100 parts by mass of the total of (A) the polymerizable monomer containing the acidic group-containing polymerizable monomer and (B) the dendritic polymer. Setting the blending amount of the acidic group-containing polymerizable monomer to 7 parts by mass or more facilitates the securement of the adhesive force to the enamel. In addition, setting the blending amount of the acidic group-containing polymerizable monomer to 60 parts by mass or less facilitates the suppression of a reduction in its adhesive force to the dentin.

In addition, the blending amount of (B) the dendritic polymer in the dental adhesive bonding material falls within preferably the range of from 5 parts by mass to 40 parts by mass, more preferably the range of from 7 parts by mass to 35 parts by mass, most preferably the range of from 10 parts by mass to 30 parts by mass with respect to 100 parts by mass of the total of (A) the polymerizable monomer containing the acidic group-containing polymerizable monomer and (B) the dendritic polymer. Setting the blending amount of the dendritic polymer to 5 parts by mass or more facilitates an additional reduction in polymerization shrinkage ratio upon curing of the dental adhesive composition. In addition, setting the blending amount of the dendritic polymer to 40 parts by mass or less prevents the deterioration of its handleability, and if needed, facilitates the securement of the mechanical strength of the dental adhesive composition.

In addition, the blending amount of (C) the water in the dental adhesive bonding material falls within preferably the range of from 2 parts by mass to 40 parts by mass, more preferably the range of from 5 parts by mass to 35 parts by mass, most preferably the range of from 7 parts by mass to 25 parts by mass with respect to 100 parts by mass of the total of (A) the polymerizable monomer containing the acidic group-containing polymerizable monomer and (B) the dendritic polymer. Setting the blending amount of the water to 2 parts by mass or more can exhibit a decalcifying force on the bonding object and can improve the penetrability into the bonding object. Accordingly, an improvement in its adhesion penetrability into the bonding object is facilitated. In addition, setting the blending amount of the water to 40 parts by mass or less facilitates the securement of its handleability and the suppression of a reduction in its adhesive force to the bonding object.

In addition, the blending amount of (D) the polymerization initiator in the dental adhesive bonding material falls within preferably the range of from 0.001 part by mass to 10 parts by mass, more preferably the range of from 0.005 part by mass to 7.5 parts by mass, most preferably the range of from 0.01 part by mass to 5 parts by mass with respect to 100 parts by mass of the total of (A) the polymerizable monomer containing the acidic group-containing polymerizable monomer and (B) the dendritic polymer. Setting the blending amount of the polymerization initiator to 0.001 part by mass or more facilitates the securement of polymerization curability upon polymerization. In addition, setting the blending amount of the polymerization initiator to 10 parts by mass or less facilitates the securement of the handleability and is excellent in terms of a cost.

It should be noted that the materials described in the foregoing may be suitably used as the polymerizable monomer containing the acidic group-containing polymerizable monomer, dendritic polymer, water, and polymerization initiator in the dental adhesive bonding material according to this embodiment, and their description is omitted here. Any other component as well as the polymerizable monomer containing the acidic group-containing polymerizable monomer, the dendritic polymer, and the water may be further added to the dental adhesive bonding material according to this embodiment as required. The bonding material may be blended with, for example, the water-soluble organic solvent, the polymerization inhibitor, or the filler as required.

—Dental Adhesive Composite Resin—

A dental adhesive composite resin (self-adhesive composite resin) according to one embodiment of the present invention includes (A) a polymerizable monomer containing an acidic group-containing polymerizable monomer, (B) a dendritic polymer, (D1) a photopolymerization initiator, and (E) a filler. The adhesive force to the tooth and adhesion durability of the dental adhesive composite resin according to this embodiment can be improved by blending the polymerizable monomer containing the acidic group-containing polymerizable monomer, the dendritic polymer, the photopolymerization initiator, and the filler in combination. This is probably because when the dendritic polymer is used, large polymerization shrinkage involved in the polymerization of the polymerizable monomer containing the acidic group-containing polymerizable monomer hardly occurs and hence the shrinkage stress of the polymerizable monomer containing the acidic group-containing polymerizable monomer is suppressed.

Accordingly, a reduction in adhesive force of the polymerizable monomer containing the acidic group-containing polymerizable monomer to the tooth, the adhesive force competing with a polymerization shrinkage stress caused upon curing of the polymerizable monomer containing the acidic group-containing polymerizable monomer at the interface with the bonding object, can be suppressed. As a result, the original adhesive force of the polymerizable monomer containing the acidic group-containing polymerizable monomer to the bonding object can be exhibited. Accordingly, high cavity compatibility is obtained upon repair of the cavity of a tooth. Further, collective filling repair of a deep cavity becomes possible.

The blending amount of the acidic group-containing polymerizable monomer in the dental adhesive composite resin falls within preferably the range of from 3 parts by mass to 38 parts by mass, more preferably the range of from 5 parts by mass to 35 parts by mass, most preferably the range of from 10 parts by mass to 30 parts by mass with respect to 100 parts by mass of the total of (A) the polymerizable monomer containing the acidic group-containing polymerizable monomer and (B) the dendritic polymer. Setting the blending amount of the acidic group-containing polymerizable monomer to 3 parts by mass or more facilitates the securement of the adhesive force of the composite resin by virtue of an action of the acidic group-containing polymerizable monomer. In addition, setting the blending amount of the acidic group-containing polymerizable monomer to 38 parts by mass or less facilitates the suppression of a reduction in adhesive force of the dental adhesive composite resin.

In addition, the blending amount of (B) the dendritic polymer in the dental adhesive composite resin falls within preferably the range of from 5 parts by mass to 40 parts by mass, more preferably the range of from 7 parts by mass to 35 parts by mass, most preferably the range of from 10 parts by mass to 30 parts by mass with respect to 100 parts by mass of the total of (A) the polymerizable monomer containing the acidic group-containing polymerizable monomer and (B) the dendritic polymer. Setting the blending amount of the dendritic polymer to 5 parts by mass or more facilitates an additional reduction in polymerization shrinkage ratio upon curing of the dental adhesive composition. In addition, setting the blending amount of the dendritic polymer to 40 parts by mass or less prevents the deterioration of its handleability, and if needed, facilitates the securement of the mechanical strength of the dental adhesive composition.

In addition, the blending amount of (D1) the photopolymerization initiator in the dental adhesive composite resin falls within preferably the range of from 0.001 part by mass to 2.5 parts by mass, more preferably the range of from 0.005 part by mass to 2 parts by mass, most preferably the range of from 0.01 part by mass to 1.75 parts by mass with respect to 100 parts by mass of the total of (A) the polymerizable monomer containing the acidic group-containing polymerizable monomer and (B) the dendritic polymer. Setting the blending amount of the photopolymerization initiator to 0.001 part by mass or more facilitates the securement of polymerization curability upon polymerization. In addition, setting the blending amount of the photopolymerization initiator to 2.5 parts by mass or less facilitates the securement of the handleability and is excellent in terms of a cost.

In addition, the blending amount of (E) the filler in the dental adhesive composite resin falls within preferably the range of from 100 parts by mass to 500 parts by mass, more preferably the range of from 150 parts by mass to 450 parts by mass, most preferably the range of from 170 parts by mass to 300 parts by mass with respect to 100 parts by mass of the total of (A) the polymerizable monomer containing the acidic group-containing polymerizable monomer and (B) the dendritic polymer. Setting the blending amount of the filler to 100 parts by mass or more facilitates the securement of the mechanical strength of a cured product of the dental adhesive composite resin. In addition, setting the blending amount of the filler to 500 parts by mass or less can secure the viscosity of the dental adhesive composite resin within a desired numerical range, and hence facilitates an improvement in its handleability and also facilitates the suppression of a reduction in its adhesive strength to the object.

It should be noted that the materials described in the foregoing may be suitably used as the polymerizable monomer containing the acidic group-containing polymerizable monomer, dendritic polymer, photopolymerization initiator, and filler in the dental adhesive composite resin according to this embodiment, and their description is omitted here. Any other component as well as the polymerizable monomer containing the acidic group-containing polymerizable monomer, the dendritic polymer, the photopolymerization initiator, and the filler may be further added to the dental adhesive composite resin according to this embodiment as required.

The composite resin may be blended with, for example, the water, the polymerization inhibitor, or the UV absorber as required. In particular, blending the water can increase the adhesive strength of the composite resin to the tooth because the blending can be expected to exhibit an improving effect on its ability to decalcify the tooth and an improving effect on its penetrability into the tooth. The blending amount of the water falls within preferably the range of from 0.2 part by mass to 15 parts by mass, more preferably the range of from 0.5 part by mass to 10 parts by mass, most preferably the range of from 1 part by mass to 7 parts by mass with respect to 100 parts by mass of the total of (A) the polymerizable monomer containing the acidic group-containing polymerizable monomer and (B) the dendritic polymer.

—Dental Adhesive Resin Cement—

A dental adhesive resin cement (self-adhesive resin cement) according to one embodiment of the present invention includes (A) a polymerizable monomer containing an acidic group-containing polymerizable monomer, (B) a dendritic polymer, (D2) a chemical polymerization initiator, and (E) a filler. The adhesive force to the bonding object, i.e., the tooth and/or a prosthesis, and adhesion durability of the dental adhesive resin cement according to this embodiment can be improved by blending the polymerizable monomer containing the acidic group-containing polymerizable monomer, the dendritic polymer, the chemical polymerization initiator, and the filler in combination. This is probably because when the dendritic polymer is used, large polymerization shrinkage involved in the polymerization of the polymerizable monomer containing the acidic group-containing polymerizable monomer hardly occurs and hence the shrinkage stress of the polymerizable monomer containing the acidic group-containing polymerizable monomer is suppressed. Accordingly, a reduction in adhesive force of the polymerizable monomer containing the acidic group-containing polymerizable monomer to the bonding object, the adhesive force competing with a polymerization shrinkage stress caused upon curing of the polymerizable monomer containing the acidic group-containing polymerizable monomer at the interface with the bonding object, can be suppressed. As a result, the original adhesive force of the polymerizable monomer containing the acidic group-containing polymerizable monomer to the bonding object can be exhibited. Accordingly, upon repair of a relatively large cavity, a prosthesis made of a metal, a ceramic, or a dental resin can be collectively fixed to the bonding object via the dental adhesive resin cement with high adhesive property and high durability.

The blending amount of the acidic group-containing polymerizable monomer in the dental adhesive resin cement falls within preferably the range of from 3 parts by mass to 38 parts by mass, more preferably the range of from 5 parts by mass to 35 parts by mass, most preferably the range of from 10 parts by mass to 30 parts by mass with respect to 100 parts by mass of the total of (A) the polymerizable monomer containing the acidic group-containing polymerizable monomer and (B) the dendritic polymer. Setting the blending amount of the acidic group-containing polymerizable monomer to 3 parts by mass or more facilitates the securement of the adhesive force of the resin cement by virtue of an action of the acidic group-containing polymerizable monomer. In addition, setting the blending amount of the acidic group-containing polymerizable monomer to 38 parts by mass or less facilitates the suppression of a reduction in adhesive force of the dental adhesive resin cement.

In addition, the blending amount of (B) the dendritic polymer in the dental adhesive resin cement falls within preferably the range of from 5 parts by mass to 40 parts by mass, more preferably the range of from 7 parts by mass to 35 parts by mass, still more preferably the range of from 10 parts by mass to 30 parts by mass, most preferably the range of from 10 parts by mass to 20 parts by mass with respect to 100 parts by mass of the total of (A) the polymerizable monomer containing the acidic group-containing polymerizable monomer and (B) the dendritic polymer. Setting the blending amount of the dendritic polymer to 5 parts by mass or more facilitates an additional reduction in polymerization shrinkage ratio upon curing of the dental adhesive resin cement. In addition, setting the blending amount of the dendritic polymer to 40 parts by mass or less prevents the deterioration of its handleability, and if needed, facilitates the securement of the mechanical strength of the dental adhesive resin cement.

In addition, the blending amount of (D2) the chemical polymerization initiator in the dental adhesive resin cement according to this embodiment falls within preferably the range of from 0.001 part by mass to 10 parts by mass, more preferably the range of from 0.005 part by mass to 7.5 parts by mass, most preferably the range of from 0.01 part by mass to 5 parts by mass with respect to 100 parts by mass of the total of (A) the polymerizable monomer containing the acidic group-containing polymerizable monomer and (B) the dendritic polymer. Setting the blending amount of the chemical polymerization initiator to 0.001 part by mass or more facilitates the securement of polymerization curability upon polymerization. In addition, setting the blending amount of the chemical polymerization initiator to 5 parts by mass or less facilitates the securement of the handleability and is excellent in terms of a cost. It should be noted that in the dental adhesive resin cement, (D1) the photopolymerization initiator may be used in combination with (D2) the chemical polymerization initiator.

In addition, the blending amount of (E) the filler in the dental adhesive resin cement falls within preferably the range of from 100 parts by mass to 500 parts by mass, more preferably the range of from 150 parts by mass to 450 parts by mass, most preferably the range of from 170 parts by mass to 300 parts by mass with respect to 100 parts by mass of the total of (A) the polymerizable monomer containing the acidic group-containing polymerizable monomer and (B) the dendritic polymer. Setting the blending amount of the filler to 100 parts by mass or more facilitates the securement of the mechanical strength of a cured product of the dental adhesive resin cement. In addition, setting the blending amount of the filler to 500 parts by mass or less can secure the viscosity of the dental adhesive resin cement within a desired numerical range, and hence facilitates an improvement in its handleability and also facilitates the suppression of a reduction in its adhesive strength to the object.

It should be noted that the materials described in the foregoing may be suitably used as the polymerizable monomer containing the acidic group-containing polymerizable monomer, dendritic polymer, chemical polymerization initiator, and filler in the dental adhesive resin cement according to this embodiment, and their description is omitted here. Any other component as well as the polymerizable monomer containing the acidic group-containing polymerizable monomer, the dendritic polymer, the chemical polymerization initiator, and the filler may be further added to the dental adhesive resin cement according to this embodiment as required.

The resin cement may be blended with, for example, the water, the polymerization inhibitor, the UV absorber, or the sulfur-containing compound as required. In particular, blending the water can increase the adhesive strength of the resin cement to the tooth because the blending can be expected to exhibit an improving effect on its ability to decalcify the tooth and an improving effect on its penetrability into the tooth. The blending amount of the water falls within preferably the range of from 0.1 part by mass to 15 parts by mass, more preferably the range of from 0.5 part by mass to 10 parts by mass, most preferably the range of from 1 part by mass to 7 parts by mass with respect to 100 parts by mass of the total of (A) the polymerizable monomer containing the acidic group-containing polymerizable monomer and (B) the dendritic polymer.

In addition, the dental adhesive resin cement according to this embodiment is typically constituted of a first component and a second component at the time of its storage, and when the cement is used, the first component and the second component are mixed. Here, the form of each of the first component and the second component may be a liquid or a paste, but in ordinary cases, both the components are particularly preferably pastes.

With regard to each constituent material constituting the dental adhesive resin cement according to this embodiment, all the kinds of constituent materials have only to be incorporated into the state of a mixture obtained by mixing the first component and the second component. That is, part of the kinds of constituent materials out of all the kinds of constituent materials constituting the dental adhesive resin cement may be incorporated into the first component, or all the kinds of constituent materials may be incorporated. It should be noted that the same holds true for the second component. Further, the above-mentioned blending amount of each constituent material constituting the dental adhesive resin cement according to this embodiment only needs to be satisfied in the state of the mixture obtained by mixing the first component and the second component. It should be noted that the blending amount of each constituent material in this case means a blending amount in the case where the dental adhesive resin cement according to this embodiment is used, and the first component and the second component are mixed in accordance with a mixing ratio (mixing ratio when using) set in advance. Here, the term "mixing ratio when using" means the following mixing ratio: when the dental adhesive resin cement according to this embodiment is a commercially available product, a mixing ratio (mixing ratio recommended by a manufacturer or a selling agency) described in the instruction, product description, or the like of the product. It should be noted that information concerning the mixing ratio when using may be, for example, that sent by mail, that delivered by an e-mail, or that provided on the web page of the manufacturer or the selling agency as well as that described in the instruction, product description, or the like attached to the product.

EXAMPLES

Hereinafter, the present invention is described in more detail by way of Examples. However, the present invention is by no means limited to Examples below.

(1) Abbreviated Names of Compounds Used in Examples and Comparative Examples

The abbreviated names of compounds used in Examples and Comparative Examples are as described below.

[(A) Polymerizable Monomer Containing Acidic Group-Containing Polymerizable Monomer]

PM:
A mixture obtained by mixing 2-methacryloyloxyethyl dihydrogen phosphate and bis(2-methacryloyloxyethyl) hydrogen phosphate at a mass ratio of 2:1

MHP:
A mixture obtained by mixing 6-methacryloxyhexyl dihydrogen phosphate and bis(2-methacryloyloxyhexyl) hydrogen phosphate at a mass ratio of 2:1

MDP:
10-Methacryloxyhexyl dihydrogen phosphate

HEMA:
2-Hydroxyethyl methacrylate

Bis-GMA:
2,2'-Bis[4-(2-hydroxy-3-methacryloxypropoxy)phenyl]propane

3G:
Triethylene glycol dimethacrylate

D2.6E:
Bismethacryloxypolyethoxyphenylpropane-bisphenol A derivative

[(B) Dendritic Polymer]

HA-DVB-500:
A hyperbranched polymer manufactured by NISSAN CHEMICAL INDUSTRIES, LTD. and having a weight-average molecular weight determined by the GPC method of 48,000. Its average hydrodynamic mean diameter is 11.7 nm (in THF). The functional group located at a terminal portion of the dendritic polymer (terminal functional group) is a methyl ester group.

HA-DMA-200:
A hyperbranched polymer manufactured by NISSAN CHEMICAL INDUSTRIES, LTD. and having a weight-average molecular weight determined by the GPC method of 22,000. Its hydrodynamic mean diameter is 5.2 nm (in THF). Its terminal functional group is a methyl ester group.

HA-DMA-50:
A hyperbranched polymer manufactured by NISSAN CHEMICAL INDUSTRIES, LTD. and having a weight-average molecular weight determined by the GPC method of 4,000. Its terminal functional group is a methyl ester group.

HA-DMA-7000:
A hyperbranched polymer manufactured by NISSAN CHEMICAL INDUSTRIES, LTD. and having a weight-average molecular weight determined by the GPC method of 67,000. Its terminal functional group is a methyl ester group.

HPS-200:
A hyperbranched polymer manufactured by NISSAN CHEMICAL INDUSTRIES, LTD. and having a weight-average molecular weight determined by the GPC method of 23,000. Its hydrodynamic mean diameter of 7.5 nm (in THF). Its terminal functional group is a styryl group.

PB:
Boltorn H20 of Perstorp, which is a hyperbranched polymer having a hydroxyl group as a terminal group (a polycondensate of dimethylolpropane whose core is trimethylolpropane and having a weight-average molecular weight determined by the GPC method of 2,100)

PBP:
A hyperbranched polymer obtained through conversion of part of the hydroxyl groups as terminal functional groups into phosphate groups by bringing diphosphorus pentoxide into contact with Boltorn H20 of Perstorp, which is a hyperbranched polymer having hydroxyl groups as terminal functional groups (a polycondensate of dimethylolpropane whose core is trimethylolpropane and having a weight-average molecular weight determined by the GPC method of 2,100) at 0° C. The ratio of terminal functional groups "hydroxy groups/phosphate groups" is 1/1.

[String-Like Polymer]
PMMA:
Non-crosslinked polymethyl methacrylate having a weight-average molecular weight determined by the GPC method of 250,000. Its terminal functional group is a methyl ester group.

[(D) Polymerization Initiator]
CQ:
Camphorquinone
BTPO:
Bis(2,4,6-trimethylbenzoyl)phenylphosphine oxide
BPO:
Benzoyl peroxide

[Amine]
DMBE: Ethyl p-N, N-dimethylaminobenzoate
DEPT: p-Tolyldiethanolamine

[(E) Filler (Filler, Particle Having No Acidic Group on its Surface)]
F1:
A filler obtained by subjecting fumed silica (having an average particle diameter of 0.01 μm) to surface treatment with methyltrichlorosilane.

F2:
A mixture obtained by mixing a product obtained by subjecting spherical silica-zirconia (having an average particle diameter of 0.4 μm) to surface treatment with γ-methacryloyloxypropyltrimethoxysilane and a product obtained by subjecting spherical silica-titania (having an average particle diameter of 0.08 μm) to surface treatment with γ-methacryloyloxypropyltrimethoxysilane at a mass ratio of 7:3

[Volatile Water-Soluble Organic Solvent]
Acetone

[Polymerization Inhibitor]
BHT:
2,6-Di-t-butyl-p-cresol (2) Evaluation Methods

[Adhesive Strength Test]
(Evaluation of Primer for its Initial Adhesive Strength)

A front tooth of a cow extracted within 24 hours after the slaughter thereof was abraded with water-resistant abrasive paper P600 under water pouring, and the plane of each of its enamel and dentin was cut out so as to be parallel to the labial surface thereof and to be flat. Next, the plane thus cut out was dried by blowing compressed air onto the plane for about 10 seconds. Next, a double-sided tape having a hole having a diameter of 3 mm was attached to the plane, and a paraffin wax having a thickness of 0.5 mm and a hole having a diameter of 8 mm was further fixed while the center of the hole of the paraffin wax was aligned with the center of the hole of the double-sided tape previously attached. Thus, a simulated cavity was formed. A primer was applied to the simulated cavity and left to stand for 20 seconds. After that, the primer was dried by blowing compressed air onto the primer for about 10 seconds. A bonding material (Scotchbond manufactured by 3M ESPE) was further applied onto the dried product and left to stand for 20 seconds. After that, the material was dried by blowing compressed air onto the material for about 10 seconds, and the dried product was further irradiated with visible light from a visible light irradiator (TOKUSO POWER LIGHT manufactured by Tokuyama Dental Corporation) for 10 seconds. A composite resin (ESTELITE SIGMA QUICK manufactured by Tokuyama Dental Corporation) was further filled into the resultant and a polyester sheet was brought into press contact therewith. After the filling, the resin was similarly cured by being irradiated with visible light for 10 seconds. Thus, an adhesion test piece was produced. It should be noted that the bonding material (Scotchbond manufactured by 3M ESPE) and composite resin (ESTELITE SIGMA QUICK manufactured by Tokuyama Dental Corporation) used here are each a dental material free of any acidic group-containing polymerizable monomer.

A resin cement (BISTITE II manufactured by Tokuyama Dental Corporation) was applied to the upper surface of the composite resin cured body of the adhesion test piece, and a cylindrical attachment made of SUS having a diameter of 8 mm and a length of 25 mm was further bonded thereto. After the resin cement had been cured at 37° C. for 15 minutes, the test piece was immersed in water at 37° C. for 24 hours. After that, the test piece was pulled with a universal tester (Autograph manufactured by Shimadzu Corporation) at a crosshead speed of 1 mm/min, and a tensile adhesive strength between the tooth and the composite resin cured body was measured. In each of Examples and Comparative Examples, the tensile adhesive strengths of four test pieces of various kinds were measured. The average of the four tensile adhesive strengths was defined as the initial adhesive strength of the corresponding example or comparative example.

(Evaluation of Bonding Material for its Initial Adhesive Strength)

As in the case of the evaluation of the primer for its initial adhesive strength, an abraded front tooth extracted from a cow was prepared, and the same simulated cavity having an adhesive surface having a diameter of 3 mm as that described above was produced by using a double-sided tape and a paraffin wax. A bonding material was applied to the simulated cavity and left to stand for 20 seconds. After that, the material was dried by blowing compressed air onto the material for about 10 seconds. The bonding material was cured by being irradiated with visible light from a visible light irradiator (TOKUSO POWER LIGHT manufactured by Tokuyama Dental Corporation) for 10 seconds. A composite resin (ESTELITE SIGMA QUICK manufactured by Tokuyama Dental Corporation) was further filled into the resultant and a polyester sheet was brought into press contact therewith. After the filling, the resin was similarly cured by being irradiated with visible light for 10 seconds. Thus, an adhesion test piece was produced. An initial adhesive strength between the tooth and the composite resin cured body was determined by using the adhesion test piece in the same manner as in the case of the evaluation of the primer for its initial adhesive strength.

(Evaluation of Composite Resin for its Initial Adhesive Strength)

As in the case of the evaluation of the primer for its initial adhesive strength, an abraded front tooth extracted from a cow was prepared, and the same simulated cavity having an adhesive surface having a diameter of 3 mm as that described above was produced by using a double-sided tape and a paraffin wax. An adhesive composite resin was filled into the simulated cavity and a polyester sheet was brought into press contact therewith. After a lapse of 30 seconds from the filling, the composite resin was cured by being irradiated with visible light from a visible light irradiator (TOKUSO POWER LIGHT manufactured by Tokuyama Dental Corporation) for 30 seconds. Thus, an adhesion test piece was produced. An initial adhesive strength between the tooth and the composite resin cured body (initial adhesive strength at a depth of the cavity of 0.5 mm) was determined by using the adhesion test piece in the same manner as in the case of the evaluation of the primer for its initial adhesive strength.

(Evaluation of Resin Cement for its Initial Adhesive Strength)

As in the case of the evaluation of the primer for its initial adhesive strength, an abraded front tooth extracted from a cow was prepared and a double-sided tape having a hole having a diameter of 3 mm was attached onto the abraded plane. Next, an A paste (first component) and B paste (second component) constituting a resin cement were collected in equal amounts in terms of a mass ratio, and were kneaded for 30 seconds to provide a mixed paste. The mixed paste was filled into the hole having a diameter of 3 mm produced with the double-sided tape, and an attachment made of SUS having a diameter of 8 mm was bonded to its upper surface. After the test piece had been held at 37° C. and a humidity of 100% for 1 hour, the dental adhesive resin cement was cured by immersing the test piece in water at 37° C. for 24 hours. Thus, an adhesion test piece was produced. An initial adhesive strength between the tooth and the resin cement cured body was determined by using the adhesion test piece in the same manner as in the case of the evaluation of the primer for its initial adhesive strength. It should be noted that in this test, a mixing ratio between the A paste (first component) and the B paste (second component) when using was set to 1:1 in terms of a mass ratio.

(Evaluation for Adhesive Strength after Durability Test)

An adhesive strength after a durability test was determined by: loading each test piece prepared in the adhesive strength test for each of the primer, the bonding material, the composite resin, and the resin cement into a thermal shock test apparatus; and performing a thermal shock test. Here, in the thermal shock test, an operation of immersing the test piece in water at 4° C. and water at 60° C. for 1 minute each was defined as one operation, and the test piece repeatedly subjected to the operation 3,000 times was measured for its adhesive strength. Then, the result of the measurement of the adhesive strength was defined as the adhesive strength after the durability test.

(Evaluations for Initial Adhesive Strength and Adhesive Strength after Durability Test in the Case where Cavity Depth is Set to 2.5 mm)

A simulated cavity having a larger depth was produced by using a paraffin wax having a thickness of 2.5 mm instead of the paraffin wax having a thickness of 0.5 mm in the evaluation of the composite resin for its initial adhesive strength. Then, an initial adhesive strength and an adhesive strength after the durability test at a cavity depth of 2.5 mm were each measured in the same manner as in the case of the evaluation of the composite resin for each of its initial adhesive strength and adhesive strength after the durability test except that this simulated cavity was used.

[Cavity Compatibility Test]

A cavity having a diameter of about 4 mm and a depth of about 2.5 mm was formed in a front tooth of a cow extracted within 24 hours after the slaughter thereof. After having been formed, the cavity was washed with water and was dried by blowing compressed air onto the cavity for about 10 seconds. A composite resin was filled into the cavity, and after a lapse of 30 seconds from the filling, the composite resin was cured by being irradiated with visible light from a visible light irradiator (TOKUSO POWER LIGHT manufactured by Tokuyama Dental Corporation) for 30 seconds. After the resultant test piece had been immersed in water at 37° C. for 24 hours, the central portion of the cavity was cut with a diamond cutter vertically to the floor surface of the cavity, and the cut surface was abraded with #1500 emery paper and then with #3000 emery paper. The abraded surface was observed with a laser microscope, and the ratio of a region where a gap was formed in an adhesive interface between the tooth and composite resin in the cavity floor portion of the formed cavity was observed. Evaluation criteria are as described below.

A: The ratio of the region where the gap is formed in the adhesive interface is less than 10%.
B: The ratio of the region where the gap is formed in the adhesive interface is 10% or more and less than 30%.
C: The ratio of the region where the gap is formed in the adhesive interface is 30% or more and less than 50%.
D: The ratio of the region where the gap is formed in the adhesive interface is 50% or more.

[Light Resistance Test]

(Evaluation of Primer for its Light Resistance)

An abraded front tooth extracted from a cow was prepared as in the case of the evaluation of the primer for its initial adhesive strength. Next, a 0.08-mm thick double-sided tape having a hole having a diameter of 4 mm was attached onto the plane of the dentin portion of the abraded front tooth of the cow, and a paraffin wax having a thickness of 0.5 mm and a hole having a diameter of 8 mm was further fixed so that the center of the hole of the double-sided tape previously attached and the center of the hole of the paraffin wax coincided with each other. Thus, a simulated cavity was formed.

A primer was applied to the simulated cavity and left to stand for 20 seconds. After that, the primer was dried by blowing compressed air onto the primer for about 10 seconds. A bonding material (Scotchbond manufactured by 3M ESPE) was further applied onto the dried product and left to stand for 20 seconds. After that, the material was dried by blowing compressed air onto the material for about 10 seconds, and the dried product was further irradiated with visible light from a visible light irradiator (TOKUSO POWER LIGHT manufactured by Tokuyama Dental Corporation) for 10 seconds. A composite resin (ESTELITE SIGMA QUICK A3 SHADE manufactured by Tokuyama Dental Corporation) was further filled into the resultant and a polyester sheet was brought into press contact therewith. After the filling, the resin was similarly cured by being irradiated with visible light for 10 seconds. Thus, an adhesion test piece was produced. It should be noted that the bonding material (Scotchbond manufactured by 3M ESPE) and composite resin (ESTELITE SIGMA QUICK manufactured by Tokuyama Dental Corporation) used here are each a dental material free of any acidic group-containing polymerizable monomer.

The adhesion test piece was loaded into a cylindrical mold having a diameter of 25 mm and a thickness of 30 mm, a normal temperature-curable embedding resin (Demotec #20 manufactured by Nano Factor Co., Ltd.) was cast into the mold, and the resin was cured. Thus, the adhesion test piece was embedded in the cured resin. The embedded product obtained by embedding the adhesion test piece with the resin was cut with a diamond cutter vertically to an adhesive interface, whereby an adhesive section was exposed. Next, a half of the exposed adhesive section was covered with aluminum foil and the resultant was exposed to pseudo-sunlight from a xenon weather meter (manufactured by Suga Test Instruments Co., Ltd., light intensity: 40 W/m$^2$) for a total of 1 hour. After that, the color tones of a primer layer portion in the portion covered with the aluminum foil (unexposed portion) and a primer layer portion in the portion exposed to the pseudo-sunlight (exposed portion) were visually observed. Evaluation criteria are as described below.

A: The color tone of the primer layer portion in the unexposed portion and the color tone of the primer layer portion in the exposed portion are substantially equal to each other.
B: There is a slight difference between the color tone of the primer layer portion in the unexposed portion and the color tone of the primer layer portion in the exposed portion.
C: There is a remarkable difference between the color tone of the primer layer portion in the unexposed portion and the color tone of the primer layer portion in the exposed portion, and the primer layer portion in the exposed portion is conspicuous.

(Evaluation of Bonding Material for its Light Resistance)

An abraded front tooth extracted from a cow was prepared as in the case of the evaluation of the primer for its initial adhesive strength. Next, a 0.08-mm thick double-sided tape having a hole having a diameter of 4 mm was attached onto the plane of the dentin portion of the abraded front tooth of the cow, and a paraffin wax having a thickness of 0.5 mm and a hole having a diameter of 8 mm was further fixed so that the center of the hole of the double-sided tape previously attached and the center of the hole of the paraffin wax coincided with each other. Thus, a simulated cavity was formed.

A bonding material was applied to the simulated cavity and left to stand for 20 seconds. After that, the material was dried by blowing compressed air onto the material for about 10 seconds. The dried product was further irradiated with visible light from a visible light irradiator (TOKUSO POWER LIGHT manufactured by Tokuyama Dental Corporation) for 10 seconds. A composite resin (ESTELITE SIGMA QUICK A3 SHADE manufactured by Tokuyama Dental Corporation) was further filled into the resultant and a polyester sheet was brought into press contact therewith. After the filling, the resin was similarly cured by being irradiated with visible light for 10 seconds. Thus, an adhesion test piece was produced. It should be noted that the composite resin (ESTELITE SIGMA QUICK manufactured by Tokuyama Dental Corporation) used here is a dental material free of any acidic group-containing polymerizable monomer.

The adhesion test piece was loaded into a cylindrical mold having a diameter of 25 mm and a thickness of 30 mm, a normal temperature-curable embedding resin (Demotec #20 manufactured by Nano Factor Co., Ltd.) was cast into the mold, and the resin was cured. Thus, the adhesion test piece was embedded in the cured resin. The embedded product obtained by embedding the adhesion test piece with the resin was cut with a diamond cutter vertically to an adhesive interface, whereby an adhesive section was exposed. Next, a half of the exposed adhesive section was covered with aluminum foil and the resultant was exposed to pseudo-sunlight from a xenon weather meter (manufactured by Suga Test Instruments Co., Ltd., light intensity: 40 W/m$^2$) for a total of 1 hour. After that, the color tones of a bonding material layer portion in the portion covered with the aluminum foil (unexposed portion) and a bonding material layer portion in the portion exposed to the pseudo-sunlight (exposed portion) were visually observed. Evaluation criteria are as described below.

A: The color tone of the bonding material layer portion in the unexposed portion and the color tone of the bonding material layer portion in the exposed portion are substantially equal to each other.
B: There is a slight difference between the color tone of the bonding material layer portion in the unexposed portion and the color tone of the bonding material layer portion in the exposed portion.
C: There is a remarkable difference between the color tone of the bonding material layer portion in the unexposed portion and the color tone of the bonding material layer portion in the exposed portion, and the bonding material layer portion in the exposed portion is conspicuous.

(Evaluation of Composite Resin for its Light Resistance)

A composite resin was filled into a 1-mm thick mold made of polyacetal having a through-hole having a diameter of 15 mm. After that, a polypropylene film was brought into press contact with each of both ends of the through-hole. Next, each of 5 sites in a circle (the central portion of the circle and positions placed near its circumference every 90° in its circumferential direction) was irradiated with light from a dental light irradiator (TOKUSO POWER LIGHT manufactured by Tokuyama Dental Corporation; optical output density: 700 mW/cm$^2$) for 10 seconds so that the entirety of the circular composite resin filled into the through-hole was irradiated with the light. Thus, a disc-like cured body (test piece) was obtained. Next, a half of the resultant test piece was covered with aluminum foil and the test piece was exposed to pseudo-sunlight from a xenon weather meter (manufactured by Suga Test Instruments Co., Ltd., light intensity: 40 W/m$^2$) for a total of 1 hour. After that, the color tones of the portion covered with the aluminum foil (unexposed portion) and the portion exposed to the pseudo-sunlight (exposed portion) were visually observed. Evaluation criteria are as described below.
A: The color tone of the unexposed portion and the color tone of the exposed portion are substantially equal to each other.
B: There is a slight difference between the color tone of the unexposed portion and the color tone of the exposed portion.
C: There is a remarkable difference between the color tone of the unexposed portion and the color tone of the exposed portion.

(Evaluation of Resin Cement for its Light Resistance)

An abraded front tooth extracted from a cow was prepared as in the case of the evaluation of the primer for its initial adhesive strength. Next, a 0.08-mm thick double-sided tape having a hole having a diameter of 4 mm was attached onto the plane of the dentin portion of the abraded front tooth of the cow. Next, an A paste (first component) and B paste (second component) constituting a resin cement were collected in equal amounts in terms of a mass ratio, and were kneaded for 30 seconds to provide a mixed paste. The mixed paste was filled into the hole having a diameter of 3 mm produced with the double-sided tape, and a cured body of a composite resin produced in advance (ESTELITE SIGMA QUICK A3 SHADE manufactured by Tokuyama Dental Corporation; cylindrical shape having a diameter of 5 mm and a thickness of 6 mm; subjected to surface treatment with TOKUSO CERAMIC PRIMER manufactured by Tokuyama Dental Corporation) was bonded to its upper surface. Next, the test piece was held at 37° C. and a humidity of 100% for 1 hour, and then the resin cement was cured by immersing the test piece in water at 37° C. for 24 hours. Thus, an adhesion test piece was produced.

The adhesion test piece was loaded into a cylindrical mold having a diameter of 25 mm and a thickness of 30 mm, a normal temperature-curable embedding resin (Demotec #20 manufactured by Nano Factor Co., Ltd.) was cast into the mold, and the resin was cured. Thus, the adhesion test piece was embedded in the cured resin. The embedded product obtained by embedding the adhesion test piece with the resin was cut with a diamond cutter vertically to an adhesive interface, whereby an adhesive section was exposed. Next, a half of the exposed adhesive section was covered with aluminum foil and the resultant was exposed to pseudo-sunlight from a xenon weather meter (manufactured by Suga Test Instruments Co., Ltd., light intensity: 40 W/m$^2$) for a total of 1 hour. After that, the color tones of a resin cement layer portion in the portion covered with the aluminum foil (unexposed portion) and a resin cement layer portion in the portion exposed to the pseudo-sunlight (exposed portion) were visually observed. Evaluation criteria are as described below.

It should be noted that in this test, a mixing ratio between the A paste (first component) and the B paste (second component) when using was set to 1:1 in terms of a mass ratio.
A: The color tone of the resin cement layer portion in the unexposed portion and the color tone of the resin cement layer portion in the exposed portion are substantially equal to each other.
B: There is a slight difference between the color tone of the resin cement layer portion in the unexposed portion and the color tone of the resin cement layer portion in the exposed portion.
C: There is a remarkable difference between the color tone of the resin cement layer portion in the unexposed portion and the color tone of the resin cement layer portion in the exposed portion, and the resin cement layer portion in the exposed portion is conspicuous.

(3) Result of Evaluation

Evaluation of Primer: Examples A1 to A10 and Comparative Examples A1 to A3

Table 1 shows the compositions of the primers used in the evaluations and Table 2 shows the results of the evaluations of the primers shown in Table 1.

Evaluation of Bonding Material: Examples B1 to B10 and Comparative Examples B1 to B3

Table 3 shows the compositions of the bonding materials used in the evaluations and Table 4 shows the results of the evaluations of the bonding materials shown in Table 3.

Evaluation of Composite Resin: Examples C1 to C13 and Comparative Examples C1 to C5

Table 5 shows the compositions of the composite resins used in the evaluations and Table 6 shows the results of the evaluations of the composite resins shown in Table 5.

Resin Cement: Examples D1 to D13 and Comparative Examples D1 to D5

Table 7 and Table 8 show the compositions of the resin cements (the A pastes and the B pastes) used in the evaluations, and Table 9 shows the results of the evaluations of the resin cements shown in Table 7 and Table 8. It should be noted that the resin cements used in the evaluations are each cured by mixing the two components, and Table 7 shows the composition of the A paste (first component) and Table 8 shows the composition of the B paste (second component). In addition, a mixing ratio between the A paste (first component) and the B paste (second component) when using is 1:1 in terms of a mass ratio.

TABLE 1

| | (A) Polymerizable monomer | | (B) Dendritic polymer (excluding Comparative Example A3) | | | | | Other component | | |
|---|---|---|---|---|---|---|---|---|---|---|
| | Acidic group-containing polymerizable monomer | Other polymerizable monomer | Kind | Weight-average molecular weight | Terminal functional group | Amount | (C) Water | Solvent | Polymerization inhibitor | Filler |
| Example A1 | PM(36) | HEMA(36)/ Bis-GMA(18) | HA-DMA-50 | 4,000 | Methyl ester group | (10) | (40) | Acetone (100) | BHT(1.0) | F1(5) |

TABLE 1-continued

| | (A) Polymerizable monomer | | (B) Dendritic polymer (excluding Comparative Example A3) | | | | (C) Water | Other component | | |
|---|---|---|---|---|---|---|---|---|---|---|
| | Acidic group-containing polymerizable monomer | Other polymerizable monomer | Kind | Weight-average molecular weight | Terminal functional group | Amount | | Solvent | Polymerization inhibitor | Filler |
| Example A2 | PM(36) | HEMA(36)/Bis-GMA(18) | HA-DMA-200 | 22,000 | Methyl ester group | (10) | (40) | Acetone (100) | BHT(1.0) | F1(5) |
| Example A3 | PM(38) | HEMA(38)/Bis-GMA(19) | HA-DVB-500 | 48,000 | Methyl ester group | (5) | (40) | Acetone (100) | BHT(1.0) | F1(5) |
| Example A4 | PM(36) | HEMA(36)/Bis-GMA(18) | HA-DVB-500 | 48,000 | Methyl ester group | (10) | (40) | Acetone (100) | BHT(1.0) | F1(5) |
| Example A5 | PM(28) | HEMA(28)/Bis-GMA(14) | HA-DVB-500 | 48,000 | Methyl ester group | (30) | (40) | Acetone (100) | BHT(1.0) | F1(5) |
| Example A6 | PM(24) | HEMA(24)/Bis-GMA(12) | HA-DVB-500 | 48,000 | Methyl ester group | (40) | (40) | Acetone (100) | BHT(1.0) | F1(5) |
| Example A7 | PM(36) | HEMA(36)/Bis-GMA(18) | HA-DMA-700 | 67,000 | Methyl ester group | (10) | (40) | Acetone (100) | BHT(1.0) | F1(5) |
| Example A8 | PM(36) | HEMA(36)/Bis-GMA(18) | HPS-200 | 23,000 | Styryl group | (10) | (40) | Acetone (100) | BHT(1.0) | F1(5) |
| Example A9 | PM(36) | HEMA(36)/Bis-GMA(18) | PB | 1,750 | Hydroxyl group | (10) | (40) | Acetone (100) | BHT(1.0) | F1(5) |
| Example A10 | PM(36) | HEMA(36)/Bis-GMA(18) | PBP | 1,750 | Phosphate group + hydroxyl group | (10) | (40) | Acetone (100) | BHT(1.0) | F1(5) |
| Comparative Example A1 | — | HEMA(70)/Bis-GMA(30) | None | — | — | 0 | (40) | Acetone (100) | BHT(1.0) | F1(5) |
| Comparative Example A2 | PM(40) | HEMA(40)/Bis-GMA(20) | None | — | — | 0 | (40) | Acetone (100) | BHT(1.0) | F1(5) |
| Comparative Example A3 | PM(36) | HEMA(36)/Bis-GMA(18) | PMMA | 250,000 | Methyl ester group | (10) | (40) | Acetone (100) | BHT(1.0) | F1(5) |

A numerical value shown in parentheses in the table means a blending amount (part(s) by mass).

TABLE 2

| | Adhesive strength to dentin (MPa) | | Light resistance test |
|---|---|---|---|
| | Initial stage | After durability test | |
| Example A1 | 9.5 | 8.2 | A |
| Example A2 | 13.7 | 11.7 | A |
| Example A3 | 12.5 | 11.0 | A |
| Example A4 | 14.4 | 12.3 | A |
| Example A5 | 15.4 | 12.7 | A |
| Example A6 | 11.3 | 9.1 | A |
| Example A7 | 14.5 | 12.0 | A |
| Example A8 | 13.8 | 11.9 | C |
| Example A9 | 12.9 | 10.0 | A |
| Example A10 | 13.4 | 11.4 | A |
| Comparative Example A1 | 0.5 | 0.1 | A |
| Comparative Example A2 | 7.4 | 5.5 | A |
| Comparative Example A3 | 8.3 | 7.1 | A |

TABLE 3

| | (A) Polymerizable monomer | | (B) Dendritic polymer (excluding Comparative Example B3) | | | | (C) Water | (D1) Polymerization initiator | | | Other component | |
|---|---|---|---|---|---|---|---|---|---|---|---|---|
| | Acidic group-containing polymerizable monomer | Other polymerizable monomer | Kind | Weight-average molecular weight | Terminal functional group | Amount | | Initiator | Amine | Solvent | Polymerization inhibitor | Filler |
| Example B1 | PM(27) | Bis-GMA(27)/3G(18)/HEMA(18) | HA-DMA-50 | 4,000 | Methyl ester group | (10) | (10) | CQ (1.2) | DMBE (1.2) | Acetone (85) | BHT(1.0) | F1(5) |
| Example B2 | PM(27) | Bis-GMA(27)/3G(18)/HEMA(18) | HA-DMA-200 | 22,000 | Methyl ester group | (10) | (10) | CQ (1.2) | DMBE (1.2) | Acetone (85) | BHT(1.0) | F1(5) |
| Example B3 | PM(28.5) | Bis-GMA(28.5)/3G(19)/HEMA(19) | HA-DVB-500 | 48,000 | Methyl ester group | (5) | (10) | CQ (1.2) | DMBE (1.2) | Acetone (85) | BHT(1.0) | F1(5) |

TABLE 3-continued

| | (A) Polymerizable monomer | | (B) Dendritic polymer (excluding Comparative Example B3) | | | | | | (D1) Polymerization initiator | | | Other component | |
|---|---|---|---|---|---|---|---|---|---|---|---|---|---|
| | Acidic group-containing polymerizable monomer | Other polymerizable monomer | Kind | Weight-average molecular weight | Terminal functional group | Amount | (C) Water | Initiator | Amine | Solvent | Polymerization inhibitor | Filler |
| Example B4 | PM(27) | Bis-GMA(27)/ 3G(18)/ HEMA(18) | HA-DVB-500 | 48,000 | Methyl ester group | (10) | (10) | CQ (1.2) | DMBE (1.2) | Acetone (85) | BHT(1.0) | F1(5) |
| Example B5 | PM(21) | Bis-GMA(21)/ 3G(14)/ HEMA(14) | HA-DVB-500 | 48,000 | Methyl ester group | (30) | (10) | CQ (1.2) | DMBE (1.2) | Acetone (85) | BHT(1.0) | F1(5) |
| Example B6 | PM(18) | Bis-GMA(18)/ 3G(12)/ HEMA(12) | HA-DVB-500 | 48,000 | Methyl ester group | (40) | (10) | CQ (1.2) | DMBE (1.2) | Acetone (85) | BHT(1.0) | F1(5) |
| Example B7 | PM(27) | Bis-GMA(27)/ 3G(18)/ HEMA(18) | HA-DMA-700 | 67,000 | Methyl ester group | (10) | (10) | CQ (1.2) | DMBE (1.2) | Acetone (85) | BHT(1.0) | F1(5) |
| Example B8 | PM(27) | Bis-GMA(27)/ 3G(18)/ HEMA(18) | HPS-200 | 23,000 | Styryl group | (10) | (10) | CQ (1.2) | DMBE (1.2) | Acetone (85) | BHT(1.0) | F1(5) |
| Example B9 | PM(27) | Bis-GMA(27)/ 3G(18)/ HEMA(18) | PB | 1,750 | Hydroxyl group | (10) | (10) | CQ (1.2) | DMBE (1.2) | Acetone (85) | BHT(1.0) | F1(5) |
| Example B10 | PM(27) | Bis-GMA(27)/ 3G(18)/ HEMA(18) | PBP | 1,750 | Phosphate group + hydroxyl group | (10) | (10) | CQ (1.2) | DMBE (1.2) | Acetone (85) | BHT(1.0) | F1(5) |
| Comparative Example B1 | — | Bis-GMA(44)/ 3G(28)/ HEMA(28) | None | — | — | 0 | (10) | CQ (1.2) | DMBE (1.2) | Acetone (85) | BHT(1.0) | F1(5) |
| Comparative Example B2 | PM(30) | Bis-GMA(30)/ 3G(20)/ HEMA(20) | None | — | — | 0 | (10) | CQ (1.2) | DMBE (1.2) | Acetone (85) | BHT(1.0) | F1(5) |
| Comparative Example B3 | PM(27) | Bis-GMA(27)/ 3G(18)/ HEMA(18) | PMMA | 250,000 | Methyl ester group | (10) | (10) | CQ (1.2) | DMBE (1.2) | Acetone (85) | BHT(1.0) | F1(5) |

A numerical value shown in parentheses in the table means a blending amount (part(s) by mass).

TABLE 4

| | Adhesive strength to dentin (MPa) | | Light resistance test |
|---|---|---|---|
| | Initial stage | After durability test | |
| Example B1 | 10.4 | 8.9 | A |
| Example B2 | 14.9 | 12.8 | A |
| Example B3 | 13.7 | 12.2 | A |
| Example B4 | 15.9 | 13.7 | A |
| Example B5 | 17.1 | 14.2 | A |
| Example B6 | 12.4 | 10.1 | A |
| Example B7 | 16.1 | 13.5 | A |
| Example B8 | 15.2 | 13.0 | C |
| Example B9 | 14.2 | 11.0 | A |
| Example B10 | 14.7 | 12.5 | A |
| Comparative Example B1 | 1.3 | 0.4 | A |
| Comparative Example B2 | 7.2 | 6.9 | A |
| Comparative Example B3 | 8.2 | 7.5 | A |

TABLE 5

| | (A) Polymerizable monomer | | (B) Dendritic polymer (excluding Comparative Example C5) | | | | | (D1) Polymerization initiator | | Other component | |
|---|---|---|---|---|---|---|---|---|---|---|---|
| | Acidic group-containing polymerizable monomer | Other polymerizable monomer | Kind | Weight-average molecular weight | Terminal functional group | Amount | (C) Water | Initiator | Amine | Polymerization inhibitor | Filler |
| Example C1 | MHP(18)/ PM(9) | Bis-GMA(45)/ 3G(18) | HA-DMA-50 | 4,000 | Methyl ester group | (10) | (0) | CQ (0.3) | DMBE (0.8) | BHT(0.3) | F2 (233) |

TABLE 5-continued

| | (A) Polymerizable monomer | | (B) Dendritic polymer (excluding Comparative Example C5) | | | | | (D1) Polymerization initiator | | Other component | |
|---|---|---|---|---|---|---|---|---|---|---|---|
| | Acidic group-containing polymerizable monomer | Other polymerizable monomer | Kind | Weight-average molecular weight | Terminal functional group | Amount | (C) Water | Initiator | Amine | Polymerization inhibitor | Filler |
| Example C2 | MHP(18)/ PM(9) | Bis-GMA(45)/ 3G(18) | HA-DMA-200 | 22,000 | Methyl ester group | (10) | (0) | CQ (0.3) | DMBE (0.8) | BHT(0.3) | F2 (233) |
| Example C3 | MHP(18)/ PM(9) | Bis-GMA(45)/ 3G(18) | HA-DMA-200 | 22,000 | Methyl ester group | (10) | (5) | CQ (0.3) | DMBE (0.8) | BHT(0.3) | F2 (233) |
| Example C4 | MHP(19)/ PM(9.5) | Bis-GMA(47.5)/ 3G(19) | HA-DVB-500 | 48,000 | Methyl ester group | (5) | (0) | CQ (0.3) | DMBE (0.8) | BHT(0.3) | F2 (233) |
| Example C5 | MHP(18)/ PM(9) | Bis-GMA(45)/ 3G(18) | HA-DVB-500 | 48,000 | Methyl ester group | (10) | (0) | CQ (0.3) | DMBE (0.8) | BHT(0.3) | F2 (233) |
| Example C6 | MHP(18)/ PM(9) | Bis-GMA(45)/ 3G(18) | HA-DVB-500 | 48,000 | Methyl ester group | (10) | (5) | CQ (0.3) | DMBE (0.8) | BHT(0.3) | F2 (233) |
| Example C7 | MHP(14)/ PM(7) | Bis-GMA(35)/ 3G(14) | HA-DVB-500 | 48,000 | Methyl ester group | (30) | (0) | CQ (0.3) | DMBE (0.8) | BHT(0.3) | F2 (233) |
| Example C8 | MHP(14)/ PM(7) | Bis-GMA(35)/ 3G(14) | HA-DVB-500 | 48,000 | Methyl ester group | (30) | (5) | CQ (0.3) | DMBE (0.8) | BHT(0.3) | F2 (233) |
| Example C9 | MHP(12)/ PM(6) | Bis-GMA(30)/ 3G(12) | HA-DVB-500 | 48,000 | Methyl ester group | (40) | (0) | CQ (0.3) | DMBE (0.8) | BHT(0.3) | F2 (233) |
| Example C10 | MHP(18)/ PM(9) | Bis-GMA(45)/ 3G(18) | HA-DMA-700 | 67,000 | Methyl ester group | (10) | (0) | CQ (0.3) | DMBE (0.8) | BHT(0.3) | F2 (233) |
| Example C11 | MHP(18)/ PM(9) | Bis-GMA(45)/ 3G(18) | HPS-200 | 23,000 | Styryl group | (10) | (0) | CQ (0.3) | DMBE (0.8) | BHT(0.3) | F2 (233) |
| Example C12 | MHP(18)/ PM(9) | Bis-GMA(45)/ 3G(18) | PB | 1,750 | Hydroxyl group | (10) | (0) | CQ (0.3) | DMBE (0.8) | BHT(0.3) | F2 (233) |
| Example C13 | MHP(18)/ PM(9) | Bis-GMA(45)/ 3G(18) | PBP | 1,750 | Phosphate group + hydroxyl group | (10) | (0) | CQ (0.3) | DMBE (0.8) | BHT(0.3) | F2 (233) |
| Comparative Example C1 | — | Bis-GMA(72)/ 3G(28) | None | — | — | 0 | (0) | CQ (0.3) | DMBE (0.8) | BHT(0.3) | F2 (233) |
| Comparative Example C2 | MHP(20)/ PM(10) | Bis-GMA(50)/ 3G(20) | None | — | — | 0 | (0) | CQ (0.3) | DMBE (0.8) | BHT(0.3) | F2 (233) |
| Comparative Example C3 | MHP(20)/ PM(10) | Bis-GMA(50)/ 3G(20) | None | — | — | 0 | (5) | CQ (0.3) | DMBE (0.8) | BHT(0.3) | F2 (233) |
| Comparative Example C4 | MHP(20)/ PM(10) | Bis-GMA(50)/ 3G(20) | None | — | — | 0 | (0) | CQ (0.3) | DMBE (0.8) | BHT(0.3) | F2 (233) |
| Comparative Example C5 | MHP(18)/ PM(9) | Bis-GMA(45)/ 3G(18) | PMMA | 250,000 | Methyl ester group | (10) | (0) | CQ (0.3) | DMBE (0.8) | BHT(0.3) | F2 (233) |

A numerical value shown in parentheses in the table means a blending amount (part (s) by mass).

TABLE 6

| | Adhesive strength to dentin (MPa) | | | | |
|---|---|---|---|---|---|
| | Depth 0.5 mm (Initial stage) | Depth 2.5 mm (Initial stage) | Depth 2.5 mm (After durability test) | Cavity compatibility | Light resistance test |
| Example C1 | 8.3 | 7.5 | 6.2 | B | A |
| Example C2 | 10.2 | 9.3 | 8.5 | A | A |
| Example C3 | 10.7 | 9.7 | 8.6 | A | A |
| Example C4 | 9.9 | 9.1 | 7.8 | B | A |
| Example C5 | 11.4 | 10.7 | 9.4 | A | A |
| Example C6 | 12.5 | 11.7 | 10.6 | A | A |
| Example C7 | 12.0 | 11.3 | 10.1 | A | A |
| Example C8 | 13.1 | 12.3 | 11.1 | A | A |
| Example C9 | 9.2 | 8.1 | 6.8 | B | A |
| Example C10 | 11.2 | 10.5 | 9.2 | A | A |
| Example C11 | 10.8 | 9.9 | 8.7 | A | C |
| Example C12 | 9.5 | 8.4 | 7.3 | B | A |
| Example C13 | 10.0 | 9.1 | 8.2 | B | A |
| Comparative Example C1 | 0.6 | 0.1 | 0.1 | D | A |
| Comparative Example C2 | 4.2 | 2.3 | 1.8 | D | A |
| Comparative Example C3 | 5.2 | 3.3 | 2.5 | D | A |
| Comparative Example C4 | 4.3 | 3.1 | 1.9 | D | A |
| Comparative Example C5 | 6.2 | 5.5 | 4.3 | C | A |

TABLE 7

| A Paste | (A) Polymerizable monomer | | (B) Dendritic polymer (excluding Comparative Example D5) | | | | (C) Water | (D1) Polymerization initiator | | Other component Polymerization | Filler |
|---|---|---|---|---|---|---|---|---|---|---|---|
| | Acidic group-containing polymerizable monomer | Other polymerizable monomer | Kind | Weight-average molecular weight | Terminal functional group | Amount | | Initiator | Peroxide | inhibitor | |
| Example D1 | MHP(30) | D2.6E(15) | HA-DMA-50 | 4,000 | Methyl ester group | (5) | (0) | CQ (0.3) | BPO (2.5) | BHT(0.15) | F2(120) |
| Example D2 | MHP(30) | D2.6E(15) | HA-DMA-200 | 22,000 | Methyl ester group | (5) | (0) | CQ (0.3) | BPO (2.5) | BHT(0.15) | F2(120) |
| Example D3 | MHP(30) | D2.6E(15) | HA-DMA-200 | 22,000 | Methyl ester group | (5) | (5) | CQ (0.3) | BPO (2.5) | BHT(0.15) | F2(120) |
| Example D4 | MHP(31.5) | D2.6E(16) | HA-DVB-500 | 48,000 | Methyl ester group | (2.5) | (0) | CQ (0.3) | BPO (2.5) | BHT(0.15) | F2(120) |
| Example D5 | MHP(30) | D2.6E(15) | HA-DVB-500 | 48,000 | Methyl ester group | (5) | (0) | CQ (0.3) | BPO (2.5) | BHT(0.15) | F2(120) |
| Example D6 | MHP(30) | D2.6E(15) | HA-DVB-500 | 48,000 | Methyl ester group | (5) | (5) | CQ (0.3) | BPO (2.5) | BHT(0.15) | F2(120) |
| Example D7 | MHP(23) | D2.6E(12) | HA-DVB-500 | 48,000 | Methyl ester group | (15) | (0) | CQ (0.3) | BPO (2.5) | BHT(0.15) | F2(120) |
| Example D8 | MHP(23) | D2.6E(12) | HA-DVB-500 | 48,000 | Methyl ester group | (15) | (5) | CQ (0.3) | BPO (2.5) | BHT(0.15) | F2(120) |
| Example D9 | MHP(20) | D2.6E(10) | HA-DVB-500 | 48,000 | Methyl ester group | (20) | (0) | CQ (0.3) | BPO (2.5) | BHT(0.15) | F2(120) |
| Example D10 | MHP(30) | D2.6E(15) | HA-DMA-700 | 67,000 | Methyl ester group | (5) | (0) | CQ (0.3) | BPO (2.5) | BHT(0.15) | F2(120) |
| Example D11 | MHP(30) | D2.6E(15) | HPS-200 | 23,000 | Styryl group | (5) | (0) | CQ (0.3) | BPO (2.5) | BHT(0.15) | F2(120) |
| Example D12 | MHP(30) | D2.6E(15) | PB | 1,750 | Hydroxyl group | (5) | (0) | CQ (0.3) | BPO (2.5) | BHT(0.15) | F2(120) |
| Example D13 | MHP(30) | D2.6E(15) | PBP | 1,750 | Phosphate group + hydroxyl group | (5) | (0) | CQ (0.3) | BPO (2.5) | BHT(0.15) | F2(120) |
| Comparative Example D1 | — | D2.6E(15)/ 3G(35) | None | — | — | 0 | (0) | CQ (0.3) | BPO (2.5) | BHT(0.15) | F2(120) |
| Comparative Example D2 | MDP(34) | D2.6E(16) | None | — | — | 0 | (0) | CQ (0.3) | BPO (2.5) | BHT(0.15) | F2(120) |
| Comparative Example D3 | MDP(34) | D2.6E(16) | None | — | — | 0 | (5) | CQ (0.3) | BPO (2.5) | BHT(0.15) | F2(120) |
| Comparative Example D4 | MDP(34) | D2.6E(16) | None | — | — | 0 | (0) | CQ (0.3) | BPO (2.5) | BHT(0.15) | F2(120) |
| Comparative Example D5 | MHP(30) | D2.6E(15) | PMMA | 250,000 | Methyl ester group | (5) | (0) | CQ (0.3) | BPO (2.5) | BHT(0.15) | F2(120) |

A numerical value shown in parentheses in the table means a blending amount (part(s) by mass).

TABLE 8

| B Paste | (A) Polymerizable monomer | | (B) Dendritic polymer (excluding Comparative Example D5) | | | | (C) Water | (D2) Polymerization initiator | | Other component Polymerization | Filler |
|---|---|---|---|---|---|---|---|---|---|---|---|
| | Acidic group-containing polymerizable monomer | Other polymerizable monomer | Kind | Weight-average molecular weight | Terminal functional group | Amount | | Initiator | Amine | inhibitor | |
| Example D1 | — | D2.6E(30)/ UDMA(15) | HA-DMA-50 | 4,000 | Methyl ester group | (5) | (0) | DMPT (1.5) | DMBE (0.8) | BHT(0.15) | F2(120) |
| Example D2 | — | D2.6E(30)/ UDMA(15) | HA-DMA-200 | 22,000 | Methyl ester group | (5) | (0) | DMPT (1.5) | DMBE (0.8) | BHT(0.15) | F2(120) |
| Example D3 | — | D2.6E(30)/ UDMA(15) | HA-DMA-200 | 22,000 | Methyl ester group | (5) | (0) | DMPT (1.5) | DMBE (0.8) | BHT(0.15) | F2(120) |
| Example D4 | — | D2.6E(31.5)/ UDMA(16) | HA-DVB-500 | 48,000 | Methyl ester group | (2.5) | (0) | DMPT (1.5) | DMBE (0.8) | BHT(0.15) | F2(120) |
| Example D5 | — | D2.6E(30)/ UDMA(15) | HA-DVB-500 | 48,000 | Methyl ester group | (5) | (0) | DMPT (1.5) | DMBE (0.8) | BHT(0.15) | F2(120) |
| Example D6 | — | D2.6E(30)/ UDMA(15) | HA-DVB-500 | 48,000 | Methyl ester group | (5) | (0) | DMPT (1.5) | DMBE (0.8) | BHT(0.15) | F2(120) |
| Example D7 | — | D2.6E(23)/ UDMA(12) | HA-DVB-500 | 48,000 | Methyl ester group | (15) | (0) | DMPT (1.5) | DMBE (0.8) | BHT(0.15) | F2(120) |

TABLE 8-continued

| | (A) Polymerizable monomer | | (B) Dendritic polymer (excluding Comparative Example D5) | | | | | (D2) Polymerization | | Other component | |
|---|---|---|---|---|---|---|---|---|---|---|---|
| B Paste | Acidic group-containing polymerizable monomer | Other polymerizable monomer | Kind | Weight-average molecular weight | Terminal functional group | Amount | Water | (C) Initiator | Amine | Polymerization inhibitor | Filler |
| Example D8 | — | D2.6E(23)/ UDMA(12) | HA-DVB-500 | 48,000 | Methyl ester group | (15) | (0) | DMPT (1.5) | DMBE (0.8) | BHT(0.15) | F2(120) |
| Example D9 | — | D2.6E(20)/ UDMA(10) | HA-DVB-500 | 48,000 | Methyl ester group | (20) | (0) | DMPT (1.5) | DMBE (0.8) | BHT(0.15) | F2(120) |
| Example D10 | — | D2.6E(30)/ UDMA(15) | HA-DMA-700 | 67,000 | Methyl ester group | (5) | (0) | DMPT (1.5) | DMBE (0.8) | BHT(0.15) | F2(120) |
| Example D11 | — | D2.6E(30)/ UDMA(15) | HPS-200 | 23,000 | Styryl group | (5) | (0) | DMPT (1.5) | DMBE (0.8) | BHT(0.15) | F2(120) |
| Example D12 | — | D2.6E(30)/ UDMA(15) | PB | 1,750 | Hydroxyl group | (5) | (0) | DMPT (1.5) | DMBE (0.8) | BHT(0.15) | F2(120) |
| Example D13 | — | D2.6E(30)/ UDMA(15) | PBP | 1,750 | Phosphate group + hydroxyl group | (5) | (0) | DMPT (1.5) | DMBE (0.8) | BHT(0.15) | F2(120) |
| Comparative Example D1 | — | D2.6E(34)/ UDMA(16) | None | — | — | 0 | (0) | DMPT (1.5) | DMBE (0.8) | BHT(0.15) | F2(120) |
| Comparative Example D2 | — | D2.6E(34)/ UDMA(16) | None | — | — | 0 | (0) | DMPT (1.5) | DMBE (0.8) | BHT(0.15) | F2(120) |
| Comparative Example D3 | — | D2.6E(34)/ UDMA(16) | None | — | — | 0 | (0) | DMPT (1.5) | DMBE (0.8) | BHT(0.15) | F2(120) |
| Comparative Example D4 | — | D2.6E(34)/ UDMA(16) | None | — | — | 0 | (0) | DMPT (1.5) | DMBE (0.8) | BHT(0.15) | F2(120) |
| Comparative Example D5 | — | D2.6E(30)/ UDMA(15) | PMMA | 250,000 | Methyl ester group | (5) | (0) | DMPT (1.5) | DMBE (0.8) | BHT(0.15) | F2(120) |

A numerical value shown in parentheses in the table means a blending amount (part(s) by mass).

TABLE 9

| | Adhesive strength to dentin (MPa) | | Light resistance test |
|---|---|---|---|
| | Initial stage | After durability test | |
| Example D1 | 7.7 | 6.7 | A |
| Example D2 | 9.6 | 8.8 | A |
| Example D3 | 10.5 | 9.1 | A |
| Example D4 | 8.9 | 8.1 | A |
| Example D5 | 11.6 | 10.3 | A |
| Example D6 | 12.1 | 10.7 | A |
| Example D7 | 11.7 | 10.4 | A |
| Example D8 | 12.6 | 11.1 | A |
| Example D9 | 8.1 | 7.3 | A |
| Example D10 | 11.4 | 10.1 | A |
| Example D11 | 10.6 | 9.5 | C |
| Example D12 | 8.5 | 7.7 | A |
| Example D13 | 9.4 | 8.6 | A |
| Comparative Example D1 | 0.5 | 0.1 | A |
| Comparative Example D2 | 4.3 | 2.3 | A |
| Comparative Example D3 | 5.5 | 3.4 | A |
| Comparative Example D4 | 5.2 | 3.5 | A |
| Comparative Example D5 | 6.5 | 5.4 | A |

(Study on Result of Evaluation)

Examples and Comparative Examples were each evaluated by the adhesive strength test method. With regard to the results of the evaluations, Examples containing the dendritic polymers were each found to be more excellent in adhesive strength than Comparative Examples were. In addition, with regard to the composite resin, Examples containing the dendritic polymers each showed an excellent result in the evaluation for cavity compatibility as well. On the other hand, each of Comparative Examples each of which is free of any dendritic polymer has a low adhesive strength and has low cavity compatibility in the case of the composite resin. In addition, Comparative Examples A1, B1, C1, and D1 each of which was free of any acidic group-containing polymerizable monomer each had a low initial adhesive strength and a low adhesive strength after the durability test. This is because none of those compositions has a decalcifying action. Further, Comparative Examples A3, B3, C5, and D5 each containing PMMA were found to have lower adhesive strengths than Examples containing the dendritic polymers did. This is probably because a string-like PMMA polymer has a low affinity for a polymerizable monomer and exhibits a small reducing effect on polymerization shrinkage.

It is assumed from the foregoing results that the incorporation of a dendritic polymer reduced the polymerization shrinkage of a polymerizable monomer. This is probably because the use of a hydrophilic dendritic polymer improved an affinity between a composition and a tooth, which led to an increase in adhesive strength.

In addition, with regard to the composite resin, Example C3, C6, or C8 containing water was additionally excellent in adhesive strength. This is probably because an improvement in penetrability into a bonding object by the incorporation of the water led to an increase in adhesive strength.

In addition, Examples and Comparative Examples were each evaluated by the light resistance test method. No large difference was observed between the results of the evaluations of Examples each containing a dendritic polymer excluding Examples each containing the dendritic polymer "HPS-200" and Comparative Examples free of any dendritic polymer. On the other hand, Examples A8, B8, C11, and D11 each using the dendritic polymer "HPS-200" having a styryl group at a terminal thereof showed poor results in light resistance. It is assumed from the foregoing results that the use of a dendritic polymer having a double bond having high reactivity like a styryl group at a terminal thereof deteriorates light resistance.

(Evaluation for Electric Conductivity)

The electric conductivities of the bonding materials of Examples B4 and B6 shown in Table 3 were measured with a pH meter (F-55 manufactured by HORIBA, Ltd.) having connected thereto an immersion-type conductivity electrode. As a result, the electric conductivity of the bonding material of Example B4 was 205 μm/cm and the electric conductivity of the bonding material of Example B6 was 296 μm/cm. On the other hand, the electric conductivity of tap water measured as a reference was from 67 to 250 μm/cm, and the electric conductivities of bonding materials obtained by setting the water contents of the bonding materials of Examples B4 and B6 to 0 parts by mass were 144 μm/cm and 95 μm/cm, respectively. Accordingly, it was found that the bonding materials of Examples B4 and B6 showed higher electric conductivities than those in the case where the bonding materials were completely free of water, and the bonding materials showed electric conductivities comparable to or more than that of tap water.

In addition, it is expected from the foregoing results that the bonding materials of Examples B1 to B3, B5, and B7 to B10 each containing water at the same ratio as those of the bonding materials of Examples B4 and B6 also show electric conductivities comparable to those of the bonding materials of Examples B4 and B6, and it is expected that the primers of Examples A1 to A10 each containing water at a ratio higher than those of the bonding materials of Examples B4 and B6 show electric conductivities comparable to or more than those of the bonding materials of Examples B4 and B6.

The invention claimed is:

1. A dental adhesive composition, comprising:
   (A) a polymerizable monomer containing an acidic group-containing polymerizable monomer;
   (B) a dendritic polymer; and
   (C) water,
   wherein (B) the dendritic polymer has a network structure including at least one kind of branching portion selected from a trifurcated branching portion and a four-furcated branching portion, and a connecting portion for connecting the branching portions,
   wherein (B) the dendritic polymer does not have an amino group, and
   wherein an electric conductivity of the dental adhesive composition is 205 μm/cm or more.

2. A dental adhesive composition according to claim 1, wherein the acidic group comprises a phosphate group.

3. A dental adhesive composition according to claim 1, wherein (B) the dendritic polymer comprises at least one kind of material selected from a dendrimer and a hyperbranched polymer, and has a weight-average molecular weight of 1,500 or more.

4. A dental adhesive composition according to claim 1, wherein (B) the dendritic polymer comprises a hyperbranched polymer containing a unit structure represented by the following general formula (I), and at least one unit structure selected from a unit structure represented by the following general formula (IIA) and a unit structure represented by the following general formula (IIB):

[Chem. 21]

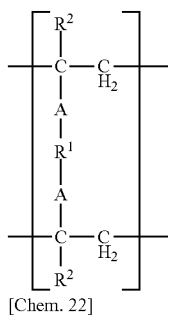

General formula (I)

[Chem. 22]

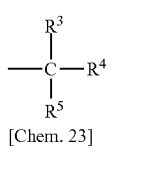

General formula (IIA)

[Chem. 23]

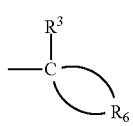

General formula (IIB)

in the general formula (I), A represents a single bond for bonding C and R1, >C=O, —O—, —COO—, or —COO—CH2-, $R^1$ represents a divalent saturated aliphatic hydrocarbon group or a divalent aromatic hydrocarbon group, and $R^2$ represents a hydrogen atom or a methyl group, in the general formula (IIA) and the general formula (IIB), $R^3$, $R^4$, and $R^5$ each represent a hydrogen atom, an alkyl group having a main chain containing 1 to 5 carbon atoms, an alkoxycarbonyl group having a main chain containing 1 to 5 carbon atoms, an aryl group, or a cyano group, and in the general formula (IIB), $R^6$ represents an alkylene group having a main chain containing 4 to 10 carbon atoms.

5. A dental adhesive composition according to claim 1, further comprising (D) a polymerization initiator.

6. A dental adhesive composition according to claim 1, further comprising (E) a filler.

7. A dental adhesive primer, comprising:
   (A) a polymerizable monomer containing an acidic group-containing polymerizable monomer;
   (B) a dendritic polymer; and
   (C) water,
   wherein (B) the dendritic polymer has a network structure including at least one kind of branching portion selected from a trifurcated branching portion and a four-furcated branching portion, and a connecting portion for connecting the branching portions,
   wherein (B) the dendritic polymer does not have an amino group, and
   wherein an electric conductivity of the dental adhesive primer is 205 μm/cm or more.

8. A dental adhesive bonding material, comprising:
   (A) a polymerizable monomer containing an acidic group-containing polymerizable monomer;
   (B) a dendritic polymer;
   (C) water; and
   (D) a polymerization initiator,
   wherein (B) the dendritic polymer has a network structure including at least one kind of branching portion selected from a trifurcated branching portion and a four-furcated branching portion, and a connecting portion for connecting the branching portions, wherein (B) the dendritic polymer does not have an amino group, and wherein an electric conductivity of the dental adhesive bonding material is 205 μm/cm or more.

9. A dental adhesive composite resin, comprising:
(A) a polymerizable monomer containing an acidic group-containing polymerizable monomer;
(B) a dendritic polymer;
(C) water;
(D1) a photopolymerization initiator; and
(E) a filler,
wherein (B) the dendritic polymer has a network structure including at least one kind of branching portion selected from a trifurcated branching portion and a four-furcated branching portion, and a connecting portion for connecting the branching portions,
wherein (B) the dendritic polymer does not have an amino group, and
wherein an electric conductivity of the dental adhesive composite resin is 205 μm/cm or more.

10. A dental adhesive resin cement, comprising:
(A) a polymerizable monomer containing an acidic group-containing polymerizable monomer;
(B) a dendritic polymer;
(C) water;
(D2) a chemical polymerization initiator; and
(E) a filler,
wherein (B) the dendritic polymer has a network structure including at least one kind of branching portion selected from a trifurcated branching portion and a four-furcated branching portion, and a connecting portion for connecting the branching portions,
wherein (B) the dendritic polymer does not have an amino group, and
wherein an electric conductivity of the dental adhesive resin cement is 205 μm/cm or more.

11. A dental adhesive composition according to claim 1, the amount of (C) the water falls within the range of from 5 parts by mass to 20 parts by mass with respect to 100 parts by mass of the oily component.

12. A dental adhesive composition, comprising:
(A) a polymerizable monomer containing an acidic group-containing polymerizable monomer; and
(B) a dendritic polymer,
wherein (B) the dendritic polymer has a network structure including at least one kind of branching portion selected from a trifurcated branching portion and a four-furcated branching portion, and a connecting portion for connecting the branching portions,
wherein (B) the dendritic polymer does not have an amino group, and
wherein the dental adhesive composition does not comprise water.

13. A dental adhesive primer according to claim 7, the amount of (C) the water falls within the range of from 5 parts by mass to 20 parts by mass with respect to 100 parts by mass of the oily component.

14. A dental adhesive bonding material according to claim 8, the amount of (C) the water falls within the range of from 5 parts by mass to 20 parts by mass with respect to 100 parts by mass of the oily component.

15. A dental adhesive composite resin according to claim 9, the amount of (C) the water falls within the range of from 5 parts by mass to 20 parts by mass with respect to 100 parts by mass of the oily component.

16. A dental adhesive composite resin, comprising:
(A) a polymerizable monomer containing an acidic group-containing polymerizable monomer;
(B) a dendritic polymer;
(D1) a photopolymerization initiator; and
(E) a filler,
wherein (B) the dendritic polymer has a network structure including at least one kind of branching portion selected from a trifurcated branching portion and a four-furcated branching portion, and a connecting portion for connecting the branching portions,
wherein (B) the dendritic polymer does not have an amino group, and
wherein the dental adhesive composite resin does not comprise water.

17. A dental adhesive resin cement according to claim 10, the amount of (C) the water falls within the range of from 5 parts by mass to 20 parts by mass with respect to 100 parts by mass of the oily component.

18. A dental adhesive resin cement, comprising:
(A) a polymerizable monomer containing an acidic group-containing polymerizable monomer;
(B) a dendritic polymer;
(D2) a chemical polymerization initiator; and
(E) a filler,
wherein (B) the dendritic polymer has a network structure including at least one kind of branching portion selected from a trifurcated branching portion and a four-furcated branching portion, and a connecting portion for connecting the branching portions,
wherein (B) the dendritic polymer does not have an amino group, and
wherein the dental adhesive resin cement does not comprise water.

19. A dental adhesive composition according to claim 1, wherein the dental adhesive composition is selected from a group consisting of (i) an oil-in-water emulsion and (ii) a composition in which an oily component, which includes (A) the polymerizable monomer containing an acidic group-containing polymerizable monomer and (B) the dendritic polymer, and (C) the water uniformly mix with each other.

20. A dental adhesive primer according to claim 7, wherein the dental adhesive primer is selected from a group consisting of (i) an oil-in-water emulsion and (ii) a composition in which an oily component, which includes (A) the polymerizable monomer containing an acidic group-containing polymerizable monomer and (B) the dendritic polymer, and (C) the water uniformly mix with each other.

21. A dental adhesive bonding material according to claim 8,
wherein the dental adhesive bonding material is selected from a group consisting of (i) an oil-in-water emulsion and (ii) a composition in which an oily component, which includes (A) the polymerizable monomer containing an acidic group-containing polymerizable monomer and (B) the dendritic polymer, and (C) the water uniformly mix with each other.

22. A dental adhesive composite resin according to claim 9,
wherein the dental adhesive composite resin is selected from a group consisting of (i) an oil-in-water emulsion and (ii) a composition in which an oily component, which includes (A) the polymerizable monomer containing an acidic group-containing polymerizable monomer and (B) the dendritic polymer, and (C) the water uniformly mix with each other.

23. A dental adhesive resin cement according to claim 10, wherein the dental adhesive resin cement is selected from a group consisting of (i) an oil-in-water emulsion and (ii) a composition in which an oily component, which includes (A) the polymerizable monomer containing an acidic group-containing polymerizable monomer and (B) the dendritic polymer, and (C) the water uniformly mix with each other.

* * * * *